United States Patent
Nishimizu et al.

(10) Patent No.: US 9,170,235 B2
(45) Date of Patent: Oct. 27, 2015

(54) EDDY CURRENT TESTING APPARATUS, EDDY CURRENT TESTING PROBE, AND EDDY CURRENT TESTING METHOD

(71) Applicant: Hitachi, Ltd., Tokyo (JP)

(72) Inventors: Akira Nishimizu, Tokyo (JP); Atsushi Ishihara, Tokyo (JP); Jun Matsumoto, Tokyo (JP); Takayuki Kawanaka, Tokyo (JP)

(73) Assignee: Hitachi, Ltd., Kanagawa (JP)

( * ) Notice: Subject to any disclaimer, the term of this patent is extended or adjusted under 35 U.S.C. 154(b) by 25 days.

(21) Appl. No.: 14/079,915

(22) Filed: Nov. 14, 2013

(65) Prior Publication Data

US 2014/0184215 A1    Jul. 3, 2014

(30) Foreign Application Priority Data

Dec. 28, 2012   (JP) ................. 2012-286535

(51) Int. Cl.
*G01N 27/82* (2006.01)
*G01N 27/90* (2006.01)

(52) U.S. Cl.
CPC ..................... *G01N 27/902* (2013.01)

(58) Field of Classification Search
CPC .................................................. G01N 27/902
USPC ................................ 324/256, 242
See application file for complete search history.

(56) References Cited

U.S. PATENT DOCUMENTS

| | | | | |
|---|---|---|---|---|
| 4,437,062 A | * | 3/1984 | Donnelly | 324/238 |
| 4,751,657 A | * | 6/1988 | Imam et al. | 702/35 |
| 5,442,285 A | * | 8/1995 | Zombo et al. | 324/227 |
| 5,442,286 A | * | 8/1995 | Sutton et al. | 324/242 |
| 6,067,844 A | * | 5/2000 | Westbrook et al. | 73/40.5 R |
| 6,952,094 B1 | * | 10/2005 | Viertl | 324/238 |
| 2003/0025496 A1 | * | 2/2003 | Trantow et al. | 324/219 |
| 2008/0265879 A1 | * | 10/2008 | Briffa et al. | 324/240 |
| 2009/0115410 A1 | * | 5/2009 | McKnight et al. | 324/240 |
| 2009/0267598 A1 | * | 10/2009 | Briffa et al. | 324/242 |
| 2011/0062954 A1 | * | 3/2011 | Cabanis et al. | 324/239 |
| 2012/0043962 A1 | * | 2/2012 | Wang et al. | 324/239 |
| 2012/0131325 A1 | * | 5/2012 | Sato | 713/100 |

* cited by examiner

*Primary Examiner* — Bot Ledynh
(74) *Attorney, Agent, or Firm* — Volpe and Koenig, P.C.

(57) ABSTRACT

An eddy current testing apparatus includes: an eddy current testing probe having an eddy current testing coil arranged on a bottom portion of a casing; a pressing mechanism configured to press the eddy current testing probe so that the bottom portion of the eddy current testing probe is placed in contact with a part of an inner wall surface of a slot formed in an object to be inspected; a carriage configured to mount the pressing mechanism and the eddy current testing probe, the carriage traveling in a depth direction of the slot; and an eddy current testing control device configured to control defect detection for the inner wall surface of the slot by acquiring a detected eddy current signal from the eddy current testing coil.

9 Claims, 16 Drawing Sheets

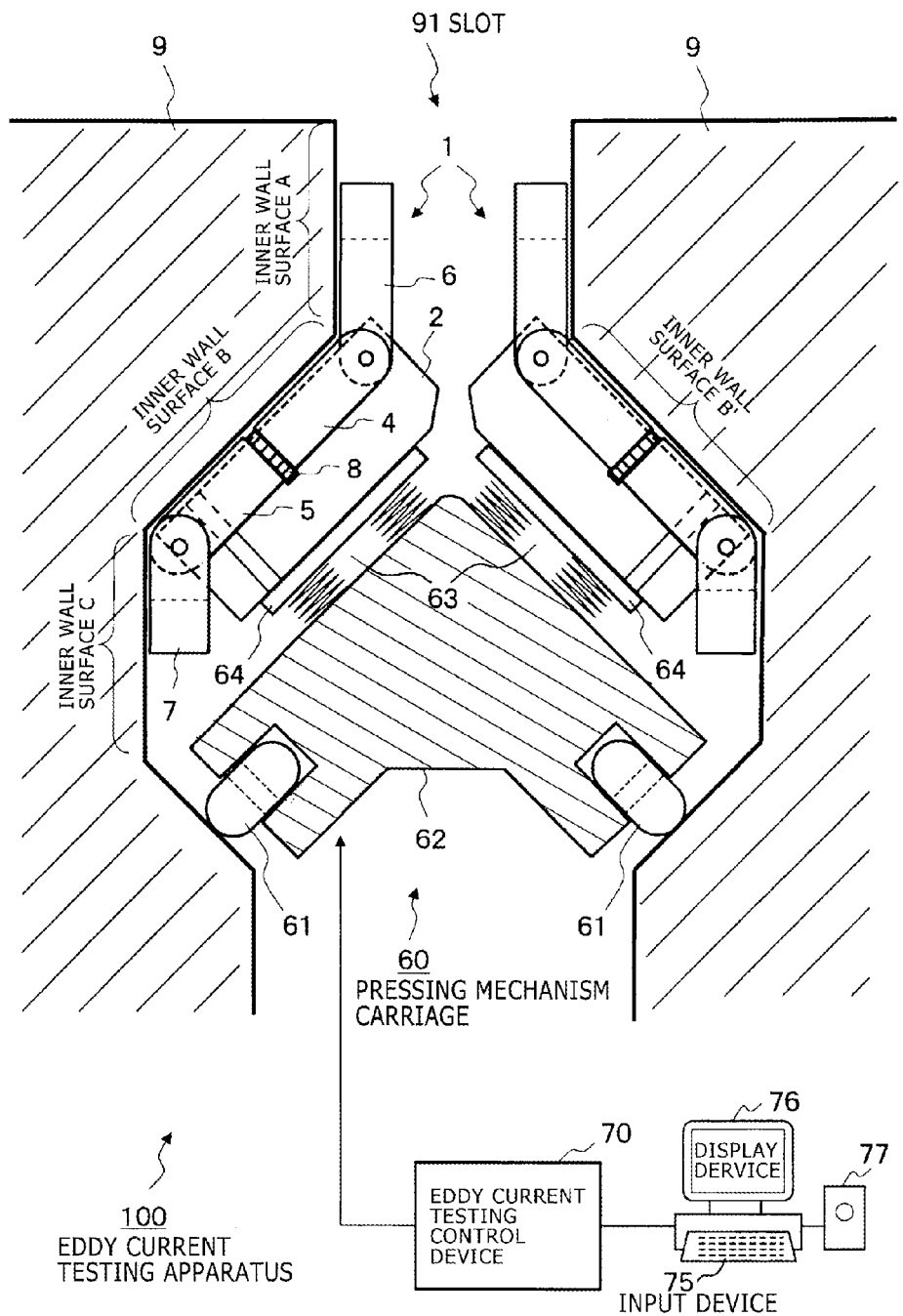

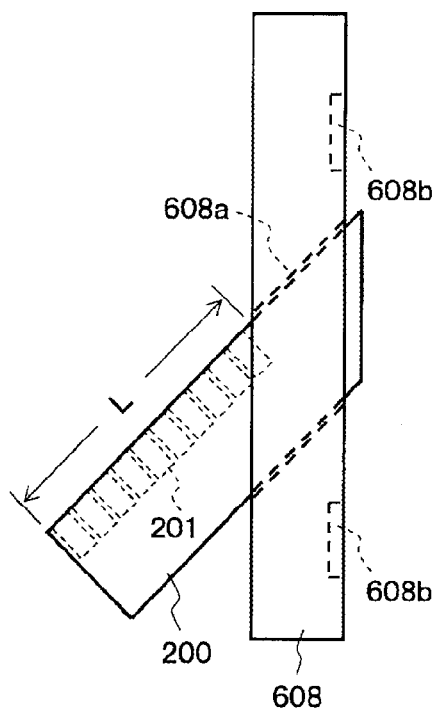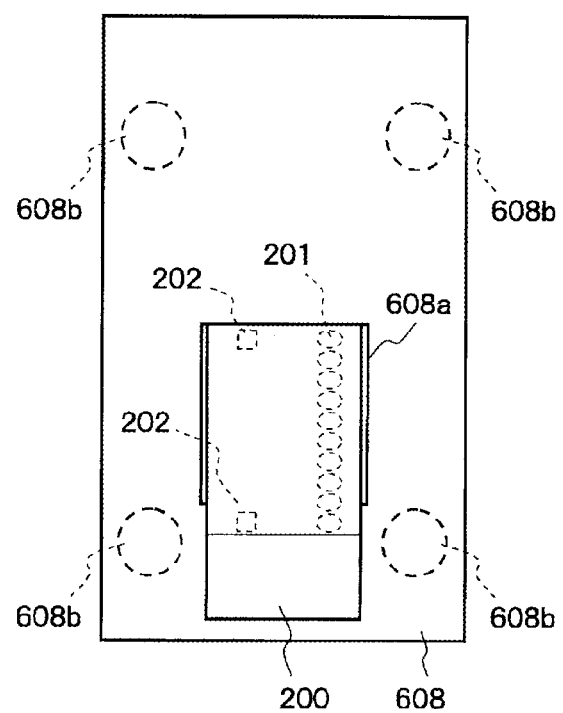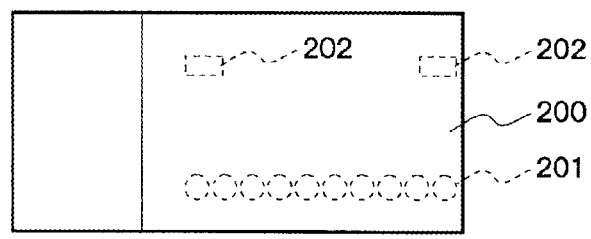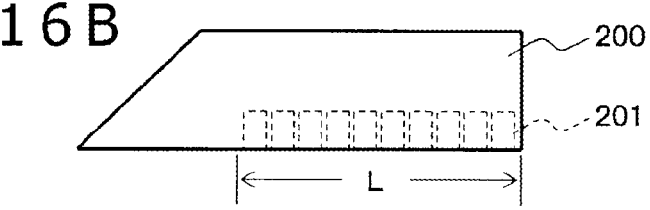

EDDY CURRENT TESTING APPARATUS, EDDY CURRENT TESTING PROBE, AND EDDY CURRENT TESTING METHOD

CLAIM OF PRIORITY

The present application claims priority from Japanese Patent applications serial No. 2012-286535, filed on Dec. 28, 2012, the respective contents of which are hereby incorporated by reference into this application.

BACKGROUND OF THE INVENTION

1. Field of the Invention

The present invention relates to an eddy current testing apparatus, an eddy current testing probe, and an eddy current testing method, which are suitable to inspect a defect on an inner wall surface of a groove-shaped portion (slot) having a large depth and the same cross-sectional shape in a depth direction.

2. Description of the Related Art

There is an eddy current testing method as a method for detecting a surface defect of an object to be inspected. In the eddy current testing method, an alternating magnetic field that is generated by a coil current is applied to the conductive object to be inspected, and disturbance of an eddy current that is induced in the object at that time is detected by a change in coil impedance, thereby evaluating whether or not a defect is present in the object to be inspected.

In recent years, eddy current testing is frequently used as a method for detecting a defect on or in an inner wall surface of a groove-shaped portion such as a blade fitting portion (also called dovetail) of a turbine disk or a slot of a rotating unit such as a generator. For example, Japanese Patent No. 4130539 discloses an example of an eddy current testing probe configured by embedding a coil in a member that conforms to a cross-sectional shape of a groove-shaped portion such as a dovetail, while the cross-sectional shape of the groove-shaped member does not change in its depth direction (length direction) or the groove-shaped member has the same cross-sectional shape in its depth direction. In addition, Japanese Patent No. 4464096 discloses an example of an eddy current testing probe configured by forming a coil-shaped wiring on a flexible printed board. The flexible printed board can be placed in contact with an inner wall surface of a groove-shaped member while conforming to a cross-sectional shape of the groove-shaped member.

SUMMARY OF THE INVENTION

The eddy current testing probe disclosed in Japanese Patent No. 4130539 is configured by the member conforming to the shape of the groove-shaped member to be inspected. If the sizes or shapes of groove-shaped members to be inspected vary, therefore, another eddy current testing probe needs to be fabricated for the groove-shaped members. This results in unnecessary cost and time for the formation of the eddy current testing probes.

In addition, the eddy current testing probe disclosed in Japanese Patent No. 4464096 is configured by the flexible and thin printed board. Thus, if the groove-shaped member to be inspected has many round shapes in cross section, the eddy current testing probe configured by the printed board can freely contact the groove-shaped member while conforming to the cross-sectional shape of the groove-shaped member to be inspected. If the groove-shaped member to be inspected has a corner in cross section, the eddy current testing probe configured by the printed board cannot exactly contact the groove-shaped member due to a limit to bending of the printed board at the corner. Thus, the accuracy of eddy current testing to be performed near the corner of the groove-shaped member to be inspected is degraded.

Defects in a groove-shaped member such as a dovetail do not uniformly occur at many parts on an inner wall surface of the groove-shaped member, but may occur at many parts to which strong forces are applied during the use of the groove-shape member. It is, therefore, sufficient if eddy current testing is performed to inspect the inner wall surface of the groove-shaped member at the parts at which the defects occur. Specifically, it is considered that if eddy current testing is performed to inspect an inner wall of a specific portion instead of all parts of the inner wall surface of the groove-shaped member, the eddy current testing probe is easily formed on the basis of the shape of the inner wall and a problem with degradation of the accuracy of eddy current testing to be performed near a corner is easily solved.

To solve the conventional technical problems, an object of the invention is to provide an eddy current testing probe, an eddy current testing apparatus, and an eddy current testing method, which can easily support a variation in a cross-sectional shape of a groove-shaped member to be inspected and suppress degradation of the accuracy of inspection to be performed near a corner in cross section.

An eddy current testing apparatus according to the invention includes an eddy current testing probe having an eddy current testing coil arranged on a bottom portion of a casing; a pressing mechanism configured to press the eddy current testing probe so that the bottom portion of the eddy current testing probe is placed in contact with a part of an inner wall surface of a slot formed in an object to be inspected; a carriage configured to mount the pressing mechanism and the eddy current testing probe, the carriage traveling in a depth direction of the slot; and an eddy current testing control device configured to control defect detection for the inner wall surface of the slot by acquiring a detected eddy current signal from the eddy current testing coil.

An eddy current testing probe according to the invention includes a first coil holding member having a plurality of eddy current testing coils arranged on a bottom portion of a casing; and a second coil holding member having one or more eddy current testing coils arranged on bottom portions of both edges of the casing, the second coil holding member being attached to contact with a side surface of the casing and the second coil holding member being detachable. In the eddy current testing probe, the second coil holding member has a length adjusting member for adjusting a distance between both end portions of the second coil holding member.

According to the invention, an eddy current testing apparatus, an eddy current testing probe, and an eddy current testing method that are capable of easily supporting a variation in a cross-sectional shape of a grooved-shaped member to be inspected and suppressing degradation of the accuracy of inspection to be performed near a corner in cross section can be provided.

BRIEF DESCRIPTION OF THE DRAWINGS

Other objects and advantages of the invention will become apparent from the following description of embodiments with reference to the accompanying drawings in which:

FIG. 9 is a diagram schematically illustrating an example of the configuration of an eddy current testing apparatus according to a second embodiment of the invention and a state in which the eddy current testing apparatus according to the second embodiment is applied to eddy current testing to be performed to inspect inner wall surfaces of the slot of the object to be inspected;

FIGS. 15A and 15B are diagrams schematically illustrating an example of a structure in which an eddy current testing probe is held by an eddy current testing probe holding member in the eddy current testing apparatus according to the third embodiment of the invention;

FIGS. 16A and 16B are top and front views schematically illustrating an example of the structure of the eddy current testing probe used by the eddy current testing apparatus according to the third embodiment of the invention.

DESCRIPTION OF THE PREFERRED EMBODIMENTS

Hereinafter, embodiments of the invention are described with reference to the accompanying drawings.

First Embodiment

Figure 1:
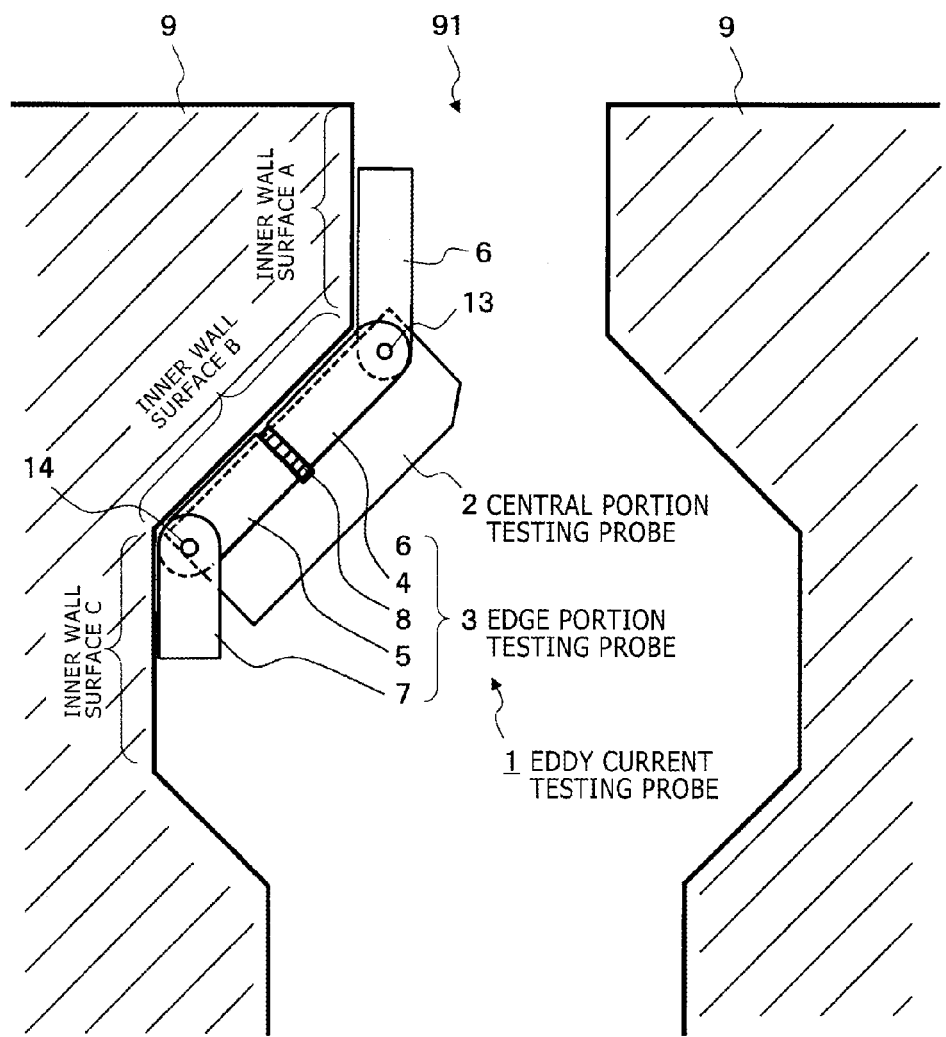
FIG. 1 is a schematic cross-sectional diagram illustrating a state in which an eddy current testing probe according to a first embodiment of the invention is placed on an inner wall surface of a slot of an object to be inspected.

FIG. 1 is a schematic cross-sectional diagram illustrating a state in which an eddy current testing probe 1 according to a first embodiment of the invention is placed on an inner wall surface of a slot 91 of an object 9 to be inspected. FIG. 1 assumes that the slot 91 is formed in a groove shape in the object 9 and is long in a depth direction (direction perpendicular to the surface of the sheet of FIG. 1). Specifically, the slot 91 is a space surrounded by a plurality of flat inner wall surfaces (inner wall surfaces A, B, C and the like) that are long in the depth direction and partitioned by a plurality of corners. It is assumed that a cross-sectional shape of the slot 91 is the same at any position in the depth direction. It is assumed that the object 9 to be inspected is, for example, a turbine disk. In this case, the slot 91 corresponds to a dovetail. If the slot 91 has a structure that is the same as or similar to the dovetail, the slot 91 is not limited to it.

In this case, the eddy current testing probe 1 according to the present embodiment is placed in contact with any of the flat inner wall surfaces of the slot 91 (the eddy current testing probe 1 is placed in contact with the inner wall surface B in the example illustrated in FIG. 1), moves on the inner wall surface (for example, the inner wall surface B) in the depth direction, and thereby performs eddy current testing to inspect a defect such as a scratch present on the surface or inside of the object 9 to be inspected.

As illustrated in FIG. 1, the eddy current testing probe 1 includes a central portion testing probe 2 and an edge portion testing probe 3. The edge portion testing probe 3 plays a role of inspecting defects at both edges of the inner wall surface (for example, the inner wall surface B) to be inspected or defects at parts near corners located in contact with other inner wall surfaces. The central portion testing probe 2 plays a role of inspecting a defect in a part that is included in the inner wall surface (for example, the inner wall surface B) except the edges to be inspected.

The edge portion testing probe 3 includes coil holding members 4, 5, corner positioning members 6, 7, and testing width adjusting members 8. The coil holding member 5 is fixed to the central portion testing probe 2 while being attachable to and detachable from the central portion testing probe 2. The coil holding members 4 are coupled to the coil holding member 5 through the testing width adjusting members 8. The corner positioning members 6, 7 are rotatable and attached to the coil holding members 4, 5 through rotary shafts 13, 14.

Figure 2A:
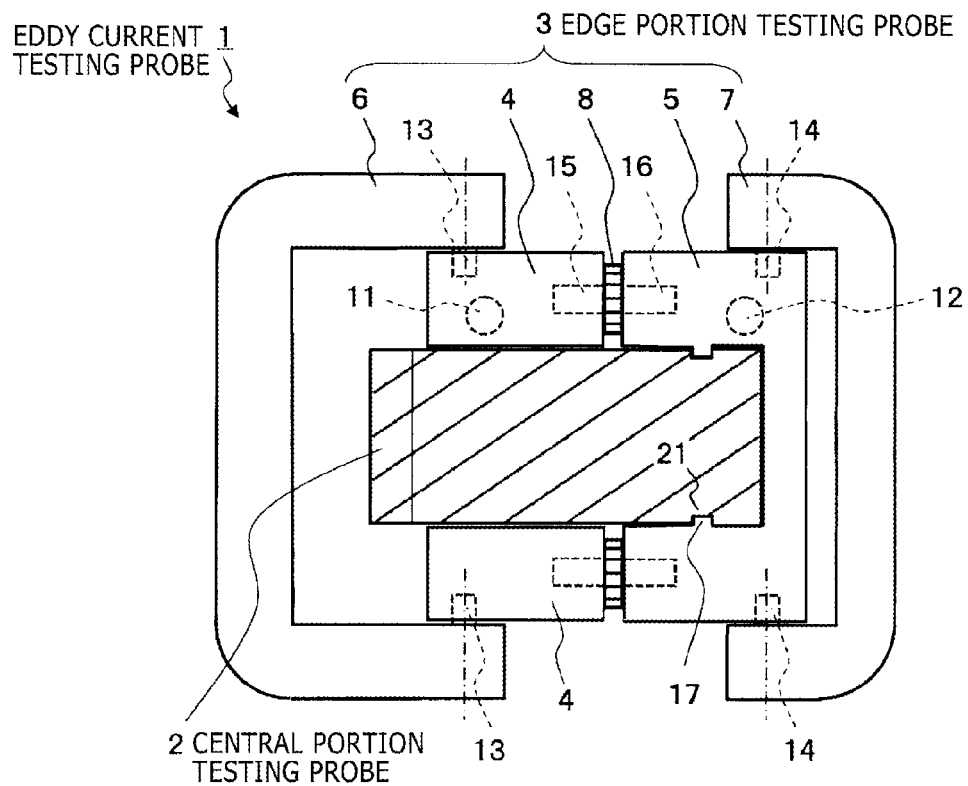
FIGS. 2A and 2B are top and side views schematically illustrating an example of the structure of the eddy current testing probe according to the first embodiment of the invention.
Figure 2B:
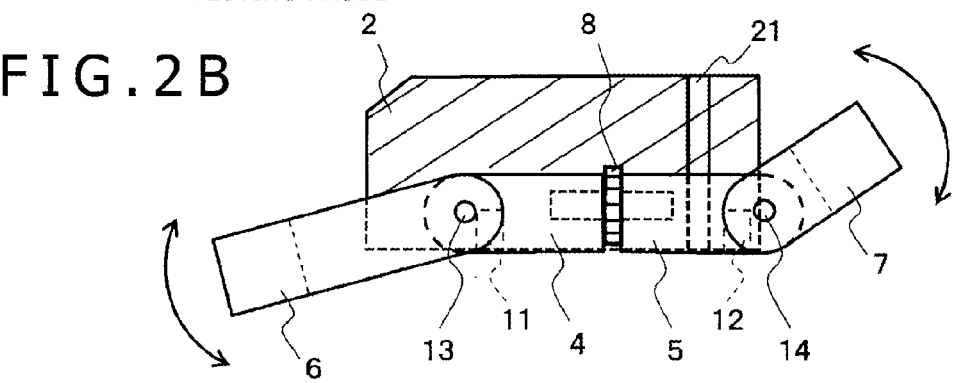
Figure 2C:
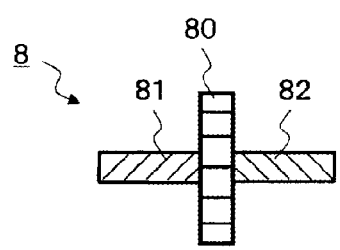
FIG. 2C is a side view of a testing width adjusting member.

FIGS. 2A and 2B are top and side views schematically illustrating an example of the structure of the eddy current testing probe 1 according to the first embodiment of the invention. FIG. 2C is a side view of the testing width adjusting members 8. The central portion testing probe 2 has a plurality of coils (not illustrated) for eddy current testing on a bottom portion of a cuboid casing. The coil holding members 4, 5, the corner positioning members 6, 7, the testing width adjusting members 8, and the like that form the edge portion testing probe 3 are arranged in contact with three side surfaces of the casing of the central portion testing probe 2. FIGS. 2A to 2C mainly describe a detailed structure of the edge portion testing probe 3, while FIGS. 3A and 3B describe a detailed structure of the central portion testing probe 2.

As illustrated in FIGS. 2A and 2B, the coil holding member 5 has a U shape when viewed from a top surface of the coil holding member 5, and an inner part of a U-shaped portion of the coil holding member 5 contacts the three side surfaces of the casing of the central portion testing probe 2. In this case, linear recessed portions 21 are formed in at least two of the side surfaces of the central portion testing probe 2 that contacts the coil holding member 5. The recessed portions 21 extend between a top surface and bottom surface of the casing of the central portion testing probe 2. Protruding portions 17 are formed in the coil holding member 5 and engaged with the recessed portions 21. The recessed portions 21 are formed as groove portions in the flat surfaces, while the protruding portions 17 are formed as protrusions on flat surfaces of the coil holding member 5.

Thus, the coil holding member 5 is fixed to the side surfaces of the casing of the central portion testing probe 2 by engaging the protruding portions 17 with the recessed portions 21 formed in the side surfaces of the casing of the central portion testing probe 2.

In this case, the coil holding member 5 is fixed by inserting the protruding portions 17 in the recessed portions 21 of the casing of the central portion testing probe 2 from an upper portion of the central portion testing probe 2 and sliding the coil holding member 5 along the recessed portions 21 toward a lower side (in a direction from the front surface to bottom surface of the sheet of FIG. 2A) so that the bottom surface of the central portion testing probe 2 matches a bottom surface of the coil holding member 5 as illustrated in FIG. 2B. Thus, the coil holding member 5 is fixed to the central portion testing probe 2 while being attachable to and detachable from the central portion testing probe 2. The bottom surfaces are surfaces that face and contact a surface to be inspected during eddy current testing.

The coil holding members 4 described in this example are two members formed in the same shape and are coupled through the testing width adjusting members 8 to both edges of the coil holding member 5 formed in the U shape. Thus, the coil holding member 5 and the two coil holding members 4 (coupled to the coil holding member 5) are formed in a horizontally long U shape, while the two coil holding members 4 are arranged in contact with the two side surfaces of the casing of the central portion testing probe 2.

The testing width adjusting members 8 each include a disk-shaped rotating portion 80 and screws 81, 82 fixed to both side surfaces of the rotating portion 80 as illustrated in FIG. 2C. The orientation of threads of the screw 81 is opposite to the orientation of threads of the screw 82. In addition, screw holes 15, 16 that are engaged with the screws 81, 82 are formed in coupling portions of the coil holding members 4 and 5 coupled to each other through the testing width adjusting members 8. Thus, distances between the coil holding members 4 and 5 can be adjusted by rotating the rotating portions 80 when necessary.

As illustrated in FIG. 2A, a coil 11 for eddy current testing is arranged at a bottom part of an edge portion that is included in at least one of the coil holding members 4 and is not coupled to the coil holding member 5. In addition, a coil 12 for eddy current testing is arranged at an edge portion included in the coil holding member 5 and located near a corner of the U-shaped portion and is different from the coil 11. Thus, a distance between the coils 11 and 12 can be adjusted by rotating the rotating portions 80 of the testing width adjusting members 8 when necessary. Although FIG. 2A illustrates only the single coil 11 and the single coil 12, a plurality of the coils 11 and a plurality of the coils 12 may be arranged.

In addition, the rotary shafts 13 are arranged in side surfaces of edge portions of the coil holding members 4, while the edge portions of the coil holding members 4 are located on the opposite side of edge portions, coupled to the coil holding member 5, of the coil holding members 4. The corner positioning member 6 that is formed in an inverted U shape is rotatable and attached to the rotary shafts 13. Similarly, the rotary shafts 14 are arranged in side surfaces of edge portions included in the coil holding member 5 and located near corners of the U-shaped portion of the coil holding member 5. The U-shaped corner positioning member 7 is rotatable and attached to the rotary shafts 14.

As illustrated in FIG. 2B, the bottom surface of the central portion testing probe 2 and the bottom surfaces of the coil holding members 4, 5 match each other and contact the same flat surface. The central portion testing probe 2 and the coil holding members 4, 5 are placed so that the bottom surface of the central portion testing probe 2 and the bottom surfaces of the coil holding members 4, 5 match each other and contact the inner wall surface (inner wall surface B in the example illustrated in FIG. 1) (to be inspected) of the slot 91 of the object 9 to be inspected. In this case, since the casing of the central portion testing probe 2 is pressed by a pressing mechanism (not illustrated) (described later) from the top surface of the casing, the bottom surface of the central portion testing probe 2 and the bottom surfaces of the coil holding members 4, 5 contact the inner wall surface (for example, the inner wall surface B) of the slot 91.

The corner positioning members 6, 7 and the testing width adjusting members 8 are used to match the distance between the coil 11 and the coil 12 with the width of the inner wall surface (for example, the inner wall surface B) to be inspected. Specifically, the distances between the coil holding members 4 and 5 are adjusted by rotating the rotating portions 80 of the testing width adjusting members 8, and bottom surfaces of the corner positioning members 6, 7 are placed in contact with inner wall surfaces (inner wall surfaces A, C in the example illustrated in FIG. 1) adjacent to the inner wall surface (for example, the inner wall surface B) to be inspected. As a result, the coils 11, 12 for eddy current testing of edges are placed at both edges of the inner wall surface (for example, the inner wall surface B) to be inspected.

Figure 3A:
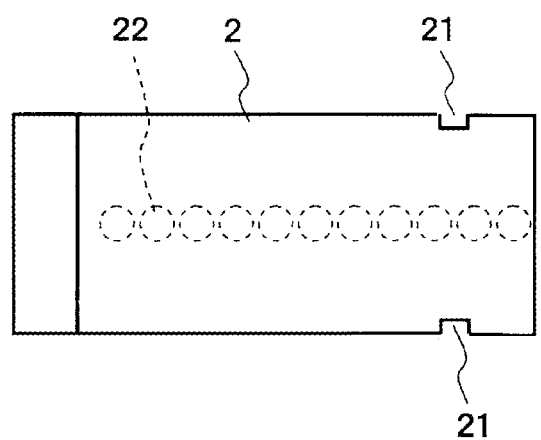
FIGS. 3A and 3B are diagrams schematically illustrating an example of the structure of a central portion testing probe included in the eddy current testing probe according to the first embodiment of the invention.
Figure 3B:
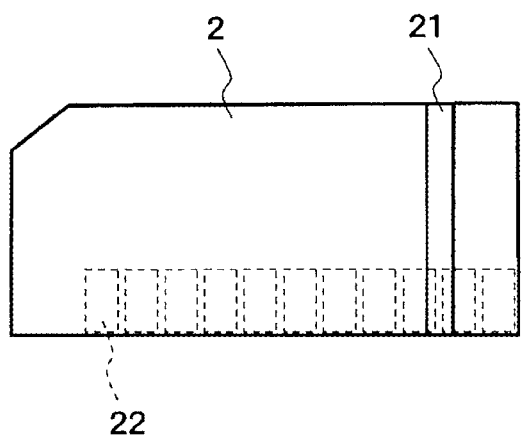

FIGS. 3A and 3B are top and front views schematically illustrating an example of the structure of the central portion testing probe 2 included in the eddy current testing probe 1 according to the first embodiment of the invention. As illustrated in FIGS. 3A and 3B, a plurality of coils 22 for eddy current testing are arranged in an array in the casing of the central portion testing probe 2 on a bottom portion of the casing of the central portion testing probe 2. As described above, the linear recessed portions 21 are formed in the side surfaces of the central portion testing probe 2 and extend between the top surface and bottom surface of the casing. The protruding portions 17 formed in the coil holding member 5 are engaged with the recessed portions 21.

The plurality of coils 22 arranged in the array and the coils 11, 12 of the edge portion testing probe 3 are each electronically switched between an exciting coil and a detecting coil, and eddy current testing is performed using the coils 22, 11, and 12. The plurality of coils 22 arranged in the array are called array coils in many cases. In FIGS. 3A and 3B, the plurality of coils 22 are arranged in the array of 1 row. The plurality of coils 22 may be two-dimensionally arranged in an array of 2 rows, 3 rows, or the like.

Figure 4:
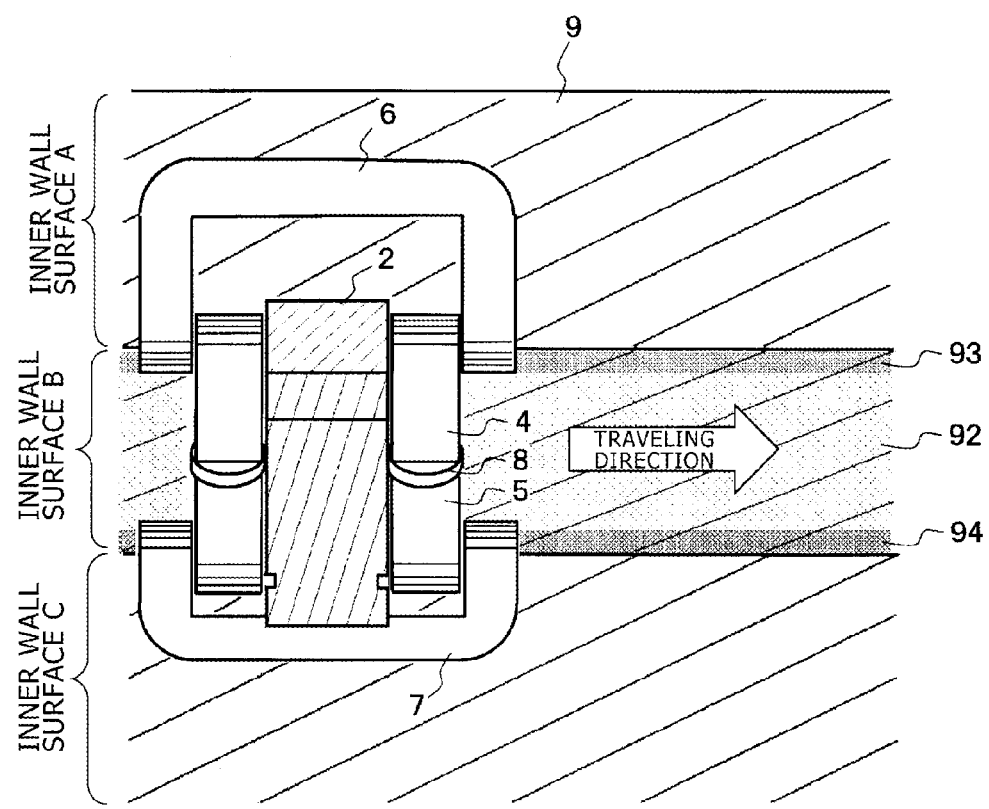
FIG. 4 is a diagram schematically illustrating a state in which the eddy current testing probe described with reference to FIGS. 1 to 3B performs eddy current testing to inspect the inner wall surface of the slot illustrated in FIG. 1.

FIG. 4 is a diagram schematically illustrating a state in which the eddy current testing probe 1 described with reference to FIGS. 1 to 3B performs eddy current testing to inspect the inner wall surface of the slot 91 illustrated in FIG. 1. In FIG. 4, the eddy current testing probe 1 performs eddy current testing to inspect the inner wall surface B of the slot 91 illustrated in FIG. 1. In this case, the eddy current testing probe 1 is moved from the left side to the right side and inspects the inner wall surface B while contacting the inner wall surface B. In the following description, eddy current testing that is performed by the eddy current testing probe 1 while the eddy current testing probe 1 contacts the inner wall surface to be inspected is referred to as "scanning" in some cases.

In FIG. 4, the coils 11, 12 of the edge portion testing probe 3 are used to perform eddy current testing to inspect corners 93, 94 that are included in the inner wall surface B and in contact with the inner wall surfaces A, C, respectively, while the plurality of coils 22 (array coils) of the central portion testing probe 2 are used to perform eddy current testing to inspect a central portion 92 of the inner wall surface B. In the present embodiment, in order to perform eddy current testing to inspect the inner wall surface B of the slot 91 to be inspected, it is sufficient if the eddy current testing probe 2 performs scanning on the inner wall surface B once while contacting the inner wall surface B.

As described above, in the embodiment, when the corner positioning members 6, 7 and the testing width adjusting members 8 are used, the distance between the coils 11 and 12 held by the coil holding members 4, 5 can be matched with the width of the inner wall surface (for example, the inner wall surface B) to be inspected. Thus, the eddy current testing probe 1 according to the present embodiment is applicable to eddy current testing to be performed to inspect the inner wall surfaces that are included in the slot 91 and have different widths and different shapes.

In the present embodiment, the maximum width among the widths of the inner wall surfaces that can be inspected by eddy current testing can be performed is determined on the basis of the number of coils 22 included in the central portion testing probe 2. Thus, if the width of the inner wall surface (for example, the inner wall surface B) to be inspected is smaller than the maximum width, eddy current testing information that is acquired from a coil 22 placed outside the central portion 92 of the inner wall surface (for example, the inner wall surface B) to be inspected is discarded.

According to the first embodiment of the invention, dependency of the eddy current testing probe 1 on the shape of the slot 91 can be reduced by providing the corner positioning members 6, 7 and the testing width adjusting members 8. The coils 11 and 12 are arranged at the edges of the coil holding members 4, 5 of the edge portion testing probe 3 in order to perform eddy current testing to inspect the edges of the inner wall surface to be inspected or the corners 93, 94. Since the edges of the coil holding members 4, 5 can reliably contact the corners 93, 94 of the inner wall surface to be inspected, degradation of the accuracy of the inspection of a part located near the corners 93, 94 can be suppressed.

In the central portion testing probe 2 according to the first embodiment of the invention, the plurality of coils 22 (array coils) arranged in the array are used to perform eddy current testing. The coils to be used to perform eddy current testing, however, are not limited to the array coils. First to fourth modified examples of the structure of the coils provided for eddy current testing in the central portion testing probe 2 are described below.

First Modified Example

Figure 5A:
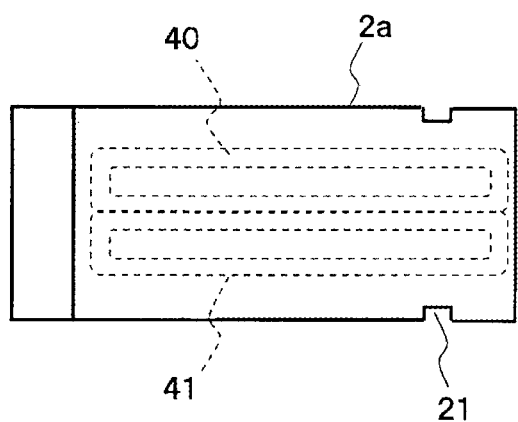
FIGS. 5A, 5B, and 5C are a top view, a front view, and a right side view that schematically illustrate an example of the structure of a central portion testing probe according to a first modified example of the first embodiment of the invention.
Figure 5B:
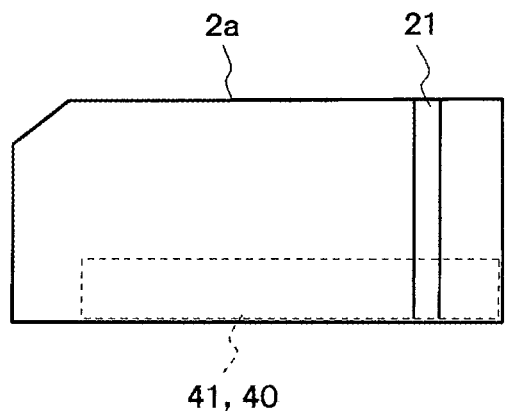
Figure 5C:
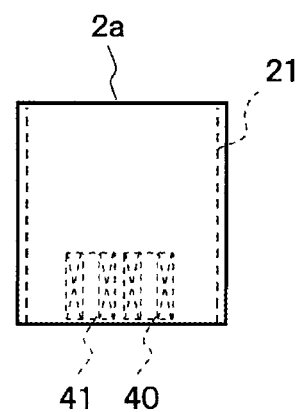

FIGS. 5A to 5C are a top view, a front view, and a right side view that schematically illustrate an example of the structure of a central portion testing probe 2a according to the first modified example of the first embodiment of the invention. As illustrated in FIGS. 5A to 5C, an exciting coil 40 and a detecting coil 41 are arranged on a bottom portion of a casing of the central portion testing probe 2a in the casing of the central portion testing probe 2a and formed in a rectangular shape (specifically, a horizontally long racetrack shape, the same applies hereinafter) and have a horizontally long cross section.

The lengths of the rectangular exciting coil 40 and detecting coil 41 are set to be longer than the width of the inner wall surface (for example, the inner wall surface B) of the slot 91 to be inspected. Thus, the eddy current testing probe 1 that uses the central portion testing probe 2a according to the first modified example can perform eddy current testing to inspect the inner wall surface (for example, the inner wall surface B) to be inspected by performing scanning once.

The exciting coil 40 and the detecting coil 41 each have a magnetic core (not illustrated), but may not have the magnetic core. The casing of the central portion testing probe 2a has the recessed portions 21 (with which the protruding portions 17 (refer to FIG. 2A) of the coil holding member 5 are engaged) formed in its side surfaces. The structure of an external configuration of the casing of the central portion testing probe 2a is the same as the structure of the casing of the central portion testing probe 2 according to the first embodiment.

Second Modified Example

Figure 6A:
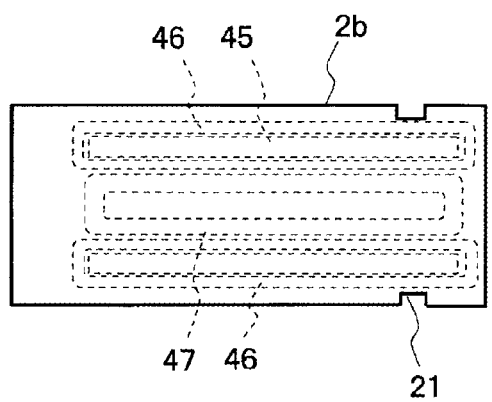
FIGS. 6A, 6B, and 6C are a top view, a front view, and a right side view that schematically illustrate an example of the structure of a central portion testing probe according to a second modified example of the first embodiment of the invention.
Figure 6B:
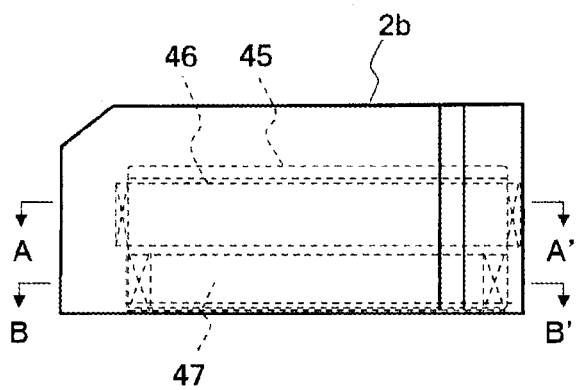
Figure 6C:
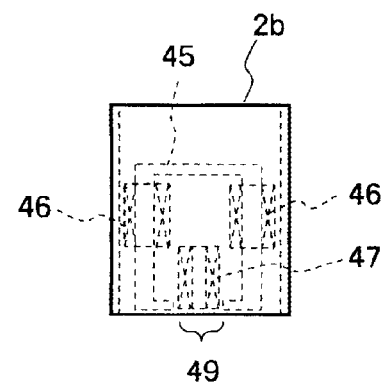

FIGS. 6A to 6C are a top view, a front view, and a right side view that schematically illustrate an example of the structure of a central portion testing probe 2b according to the second modified example of the first embodiment of the invention. As illustrated in FIGS. 6A to 6C, a magnetic core 45, an exciting coil 46, and a detecting coil 47 are arranged in a casing of the central portion testing probe 2b. The magnetic core 45 has a gap 49. The exciting coil 46 is wound around the magnetic core 45. The detecting coil 47 is arranged at the gap 49. The top view of FIG. 6A illustrates the central portion testing probe 2b by overlapping a cross-sectional structure taken along a line A-A' of the front view of FIG. 6B with a cross-sectional structure taken along a line B-B' of the front view of FIG. 6B.

In the second modified example, the exciting coil 46 and the detecting coil 47 are each formed in a horizontally long rectangular shape. The lengths of the exciting coil 46 and detecting coil 47 in a horizontal direction are set to be longer than the width of the inner wall surface (for example, the inner wall surface B illustrated in FIG. 1) that is included in the slot 91 and to be inspected. Thus, the eddy current testing probe 1 that uses the central portion testing probe 2b according to the second modified example can perform eddy current testing to inspect the inner wall surface (for example, the inner wall surface B) to be inspected by performing scanning once.

The casing of the central portion testing probe 2b has the recessed portions 21 (with which the protruding portions 17 (refer to FIG. 2A) of the coil holding member 5 are engaged) formed in its side surfaces. The structure of an external configuration of the casing of the central portion testing probe 2*b* is the same as the structure of the casing of the central portion testing probe 2 according to the first embodiment.

Third Modified Example

Figure 7A:
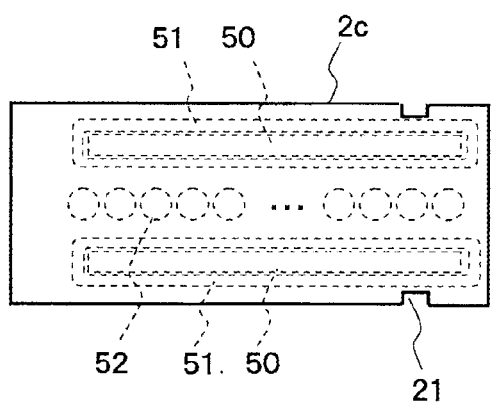
FIGS. 7A, 7B, and 7C are a top view, a front view, and a right side view that schematically illustrate an example of the structure of a central portion testing probe according to a third modified example of the first embodiment of the invention.
Figure 7B:
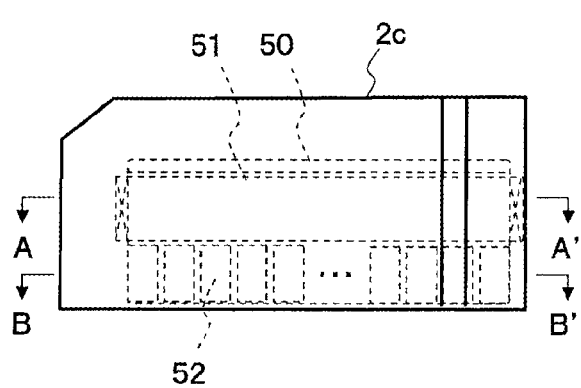
Figure 7C:
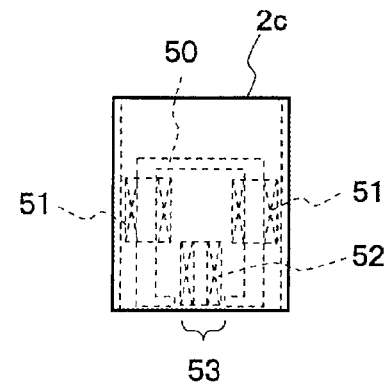

FIGS. 7A to 7C are a top view, a front view, and a right side view that schematically illustrate an example of the structure of a central portion testing probe 2*c* according to the third modified example of the first embodiment of the invention. As illustrated in FIGS. 7A to 7C, a magnetic core 50, an exciting coil 51, and a plurality of detecting coils 52 are arranged in the central portion testing probe 2*c*. The magnetic core 50 has a gap 53. The exciting coil 51 is wound around the magnetic core 50. The plurality of detecting coils 52 are arranged in an array at the gap 53. The top view of FIG. 7A illustrates the central portion testing probe 2*c* by overlapping a cross-sectional structure taken along a line A-A' of the front view of FIG. 7B with a cross-sectional structure taken along a line B-B' of the front view of FIG. 7B.

In the third modified example, the exciting coil 51 is formed in the horizontally long rectangular shape, and the length of the exciting coil 51 in the horizontal direction is set to be longer than the width of the inner wall surface (for example, the inner wall surface B illustrated in FIG. 1) included in the slot 91 and to be inspected. The diameters and number of detecting coils 52 are determined on the basis of the length. Thus, the eddy current testing probe 1 that uses the central portion testing probe 2*c* according to the third modified example can perform eddy current testing to inspect the inner wall surface (for example, the inner wall surface B) to be inspected by performing scanning once.

The casing of the central portion testing probe 2*c* has the recessed portions 21 (with which the protruding portions 17 (refer to FIG. 2A) of the coil holding member 5 are engaged) formed in its side surfaces. The structure of an external configuration of the casing of the central portion testing probe 2*c* is the same as the structure of the casing of the central portion testing probe 2 according to the first embodiment.

Fourth Modified Example

Figure 8A:
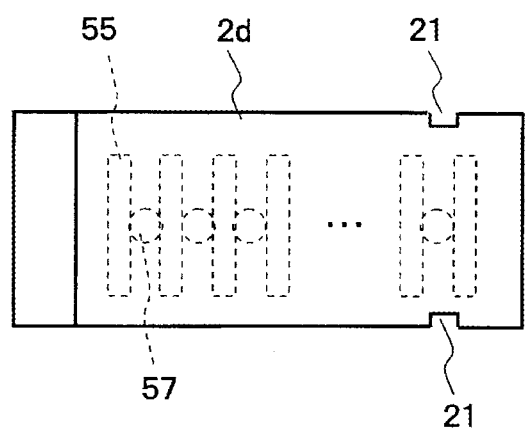
FIGS. 8A and 8B are top and front views schematically illustrating an example of the structure of a central portion testing probe according to a fourth modified example of the first embodiment of the invention.
Figure 8B:
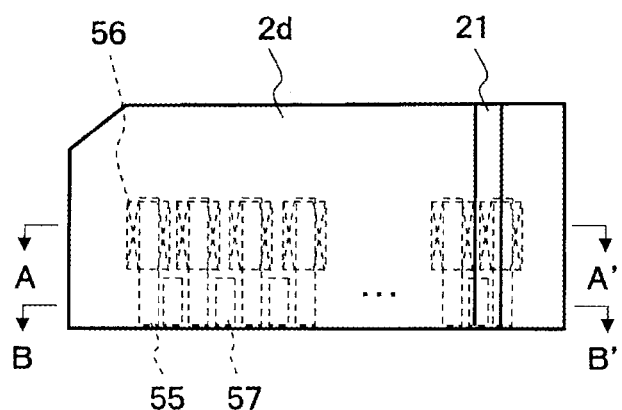

FIGS. 8A and 8B are top and front views schematically illustrating an example of the structure of a central portion testing probe 2*d* according to a fourth modified example of the first embodiment of the invention. As illustrated in FIGS. 8A and 8B, a plurality of exciting coils 56 and a plurality of detecting coils 57 are arranged in a casing of the central portion testing probe 2*d*. The exciting coils 56 are wound around magnetic cores 55 and arranged at regular intervals, while each of the detecting coils 57 is arranged between two exciting coils 56 adjacent to the detecting coil 57. The top view of FIG. 8A illustrates the central portion testing probe 2*d* by overlapping a cross-sectional structure taken along a line A-A' of the front view of FIG. 7B with a cross-sectional structure taken along a line B-B' of the front view of FIG. 7B. In the top view of FIG. 8A, an illustration of the exciting coils 56 is omitted (only the magnetic cores 55 are illustrated).

The exciting coils 56 are formed in a rectangular shape and arranged so that long surfaces of the exciting coils 56 face each other. In this case, a direction in which the detecting coils 57, each of which is arranged between two exciting coils 56 adjacent to the detecting coil 57, are arranged is nearly perpendicular to a longitudinal direction of the exciting coils 56 formed in the rectangular shape. In FIGS. 8A and 8B, the total length of a region in which the exciting coils 56 and the detecting coils 57 are arranged is set to be longer than the width of the inner wall surface (for example, the inner wall surface B illustrated in FIG. 1) included in the slot 91 and to be inspected. Thus, the eddy current testing probe 1 that uses the central portion testing probe 2*d* according to the fourth modified example can perform eddy current testing to inspect the inner wall surface (for example, the inner wall surface B) to be inspected by performing scanning once.

The casing of the central portion testing probe 2*d* has the recessed portions 21 (with which the protruding portions (refer to FIG. 2A) of the coil holding member 5 are engaged) formed in its side surfaces. The structure of an external configuration of the casing of the central portion testing probe 2*d* is the same as the structure of the casing of the central portion testing probe 2 according to the first embodiment.

In the first to fourth modified examples, the edge portion testing probe 3 is used in the same manner as the first embodiment. It is, therefore, apparent that effects that are the same as or similar to the first embodiment can be obtained in the first to fourth modified examples.

Second Embodiment

FIG. 9 is a diagram schematically illustrating an example of the configuration of an eddy current testing apparatus 100 according to a second embodiment of the invention and a state in which the eddy current testing apparatus 100 is applied to eddy current testing to be performed to inspect inner wall surfaces of the slot 91 of the object 9 to be inspected. As illustrated in FIG. 9, the eddy current testing apparatus 100 according to the second embodiment of the invention includes the eddy current testing probes 1 described in the first embodiment, a pressing mechanism carriage 60, and an eddy current testing control device 70. The pressing mechanism carriage 60 has a mechanism for pressing the bottom portions of the eddy current testing probes 1 against inner wall surfaces to be inspected. The eddy current testing control device 70 controls acquisition of eddy current testing data during eddy current testing.

In the example illustrated in FIG. 9, the eddy current testing apparatus 100 has the two eddy current testing probes 1 in order to perform eddy current testing to inspect inner wall surfaces B and B' of the slot 91.

The pressing mechanism carriage 60 has wheels 61 and includes a traveling carriage 62 and pressing plates 64. The traveling carriage 62 travels in the slot 91 of the object 9 to be inspected. The pressing plates 64 are attached to the traveling carriage 62 through spring members 63 and press the eddy current testing probes 1 against the inner wall surfaces to be inspected. In this case, the spring members 63 and the pressing plates 64 correspond to the pressing mechanism.

In the example illustrated in FIG. 9, the traveling carriage 62 has the plurality of wheels 61 in order to ensure stable traveling, preferably has four wheels 61. In addition, the two pressing plates 64 are arranged in order to press the two eddy current testing probes 1 against the different inner wall surfaces B and B'.

The traveling carriage 62 is held through the plurality of wheels 61 by inner wall surfaces of the slot 91 that are not the inner wall surfaces to be inspected and presses the two eddy current testing probes 1 through the two pressing plates 64 against the inner wall surfaces B and B' to be inspected. Thus, the eddy current testing apparatus 100 can perform eddy current testing to inspect the inner wall surfaces B and B' (to be inspected) simultaneously by causing the traveling carriage 62 to travel in the slot 91 in the depth direction (direction from the front surface to back surface of the sheet of FIG. 9) once.

When the traveling carriage 62 travels in the slot 91, the two eddy current testing probes 1 pressed against the inner wall surfaces B and B' slide on the inner wall surfaces B and B'. It is, therefore, necessary that a frictional force applied during the slide be sufficiently lower than frictional forces applied between the pressing forces 64 and the eddy current testing probes 1. Thus, pressing surfaces of the pressing plates 64 and/or the top surfaces, contacting the pressing plates 64, of the central portion testing probes 2 are made of an adhesive member such as rubber.

In FIG. 9, pressing forces of the pressing plates 64 are generated using the spring members 63 such as springs. The pressing forces of the pressing plates 64 may be generated using balloons in which air is injected, instead of the spring members 63.

The eddy current testing control device 70 may be a personal computer that includes an input device 75 (such as a keyboard, a mouse, a touch panel or the like), a display device 76 (such as a liquid crystal display device), and an audio output device 77 (such as a speaker). Although the eddy current testing control device 70 is connected to the eddy current testing probes 1 and the pressing mechanism carriage 60, an illustration of wirings for the connections is omitted in FIG. 9.

Figure 10:
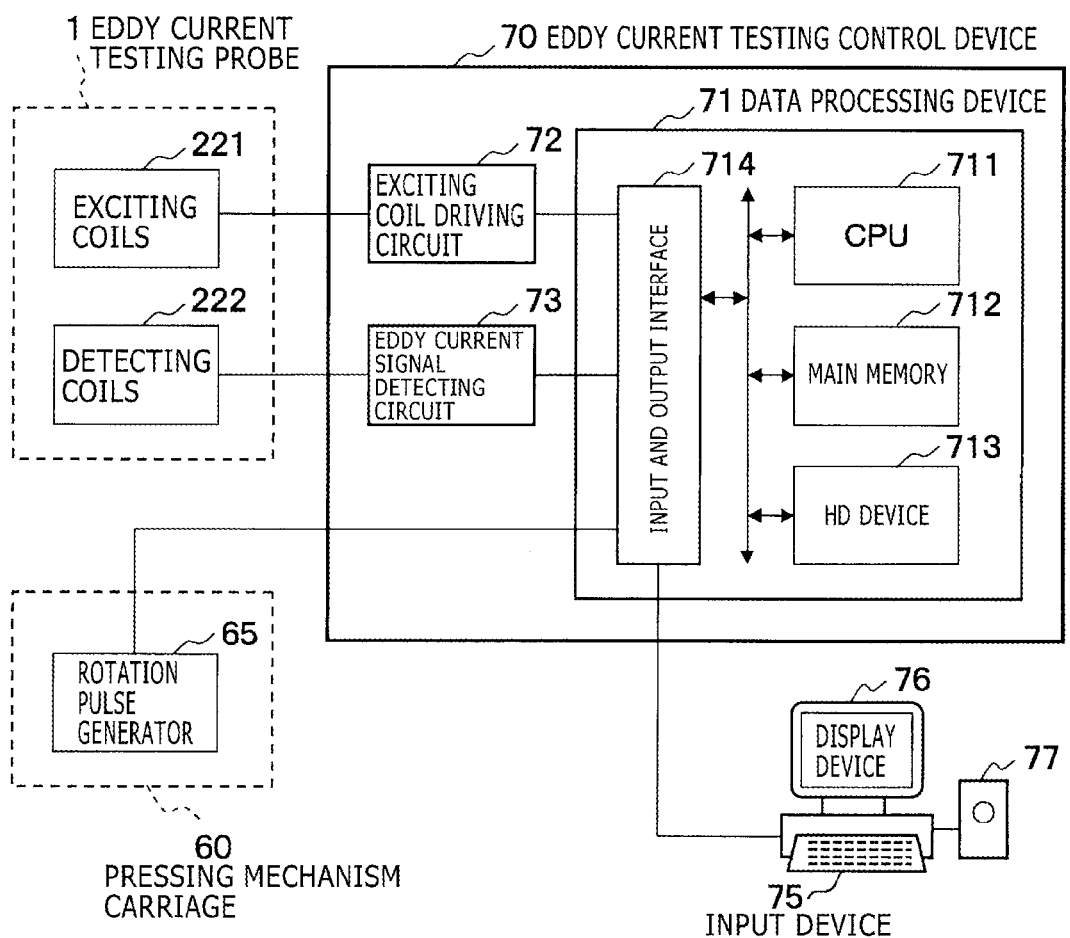
FIG. 10 is a diagram illustrating an example of the configuration of an eddy current testing control device according to the second embodiment of the invention.

FIG. 10 is a diagram illustrating an example of the configuration of the eddy current testing control device 70 according to the second embodiment of the invention. As illustrated in FIG. 10, the eddy current testing control device 70 includes a data processing device 71, an exciting coil driving circuit 72, and an eddy current signal detecting circuit 73. The eddy current testing control device 70 is connected to the eddy current testing probes 1, the pressing mechanism carriage 60, the input device 75, the display device 76, and the like.

The data processing device 71 includes a central processing unit (CPU) 711, a main memory 712, a hard disk (HD) device 713, and an input and output interface 714, like a general personal computer. The data processing device 71 has control functions for eddy current testing. The control functions are achieved by causing the CPU 711 to execute a program stored in the main memory 712 or the HD device 713.

The exciting coil driving circuit 72 is connected to the data processing device 71 and exciting coils 221 included in the eddy current testing probes 1. The exciting coil driving circuit 72 supplies an alternating current of a predetermined frequency (of, for example, 20 kHz) to the exciting coils 221 on the basis of an instruction from the data processing device 71. The eddy current signal detecting circuit 73 is connected to the data processing device 71 and detecting coils 222 and detects values of impedance of the detecting coils 222 or converted voltage values of the detecting coils 222.

As described above, the coils 22 (refer to FIG. 3) arranged in the array may be used as the exciting coils 221 or the detecting coils 222 while being electronically switched between the exciting coils 221 and the detecting coils 222. In this case, the coils 22 are connected to the exciting coil driving circuit 72 and the eddy current signal detecting circuit 73 through an electronic switching circuit (not illustrated).

In FIG. 10, the exciting coil driving circuit 72 and the eddy current signal detecting circuit 73 are arranged in the same board or casing. The exciting coil driving circuit 72 and the eddy current signal detecting circuit 73, however, are not limited to this configuration. The exciting coil driving circuit 72 and the eddy current signal detecting circuit 73 may be arranged in each of the eddy current testing probes 1. In this case, the data processing device 71 may be wirelessly connected to the exciting coil driving circuits 72 and the eddy current signal detecting circuits 73.

A rotation pulse generator 65 that generates a pulse signal when the wheels 61 rotate at a predetermined angle is provided for the wheels 61 of the pressing mechanism carriage 60 (refer to FIG. 9). The rotation pulse generator 65 is a rotary encoder or the like. The pulse signal and data of rotational angles are input to the data processing device 71. Thus, the CPU 711 of the data processing device 71 calculates a travel distance of the traveling carriage 62 or the position of the traveling carriage 62 on the basis of the number of the pulse signals, the rotational angles, the diameter of the wheels 61, and the like.

The traveling carriage 62 has a motor that rotates on the basis of an instruction from the data processing device 71. The traveling carriage 62 may automatically travel or may travel without the motor by being pushed and pulled by an operator using his or her hand, a bar, or the like.

Figure 11:
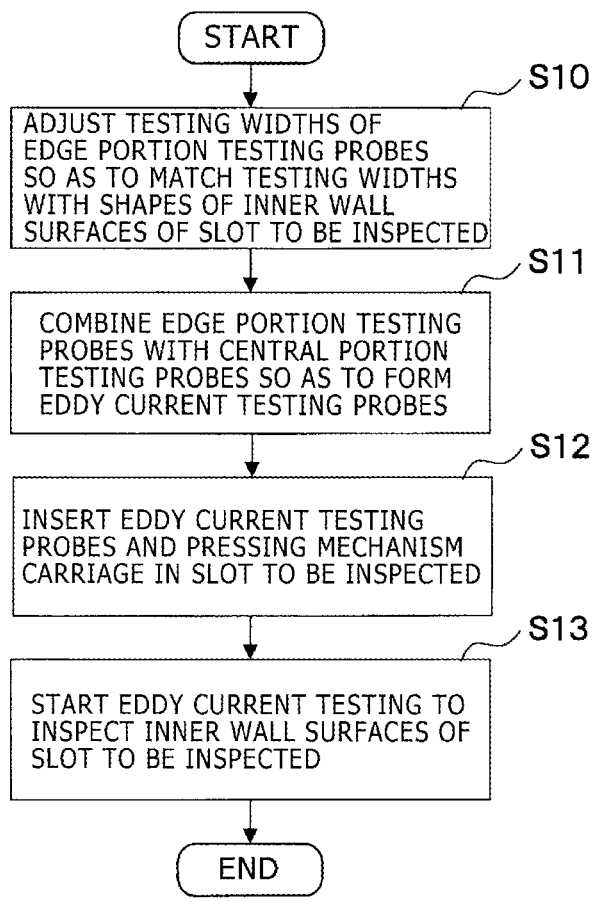
FIG. 11 is a flowchart of an example of an operational procedure required to perform eddy current testing to inspect the inner wall surfaces of the slot using the eddy current testing apparatus according to the second embodiment of the invention.

FIG. 11 is a flowchart of an example of an operational procedure required to perform eddy current testing to inspect the inner wall surfaces of the slot 91 using the eddy current testing apparatus 100 according to the second embodiment of the invention. At the start time of this operation, the central portion testing probe 2 is separated from the edge portion testing probe 3 in each of the eddy current testing probes 1 to be used for eddy current testing. The operational procedure is described below in detail with reference to FIG. 9 and the like.

As illustrated in FIG. 11, the operator adjusts testing widths of the edge portion testing probes 3 so that the testing widths match the inner wall surfaces of the slot 91 to be inspected (in step S10). Specifically, the operator manually presses the bottom surfaces of the coil holding members 4, 5 of the edge portion testing probes 3 against the inner wall surfaces (inner wall surfaces B, B' in the example illustrated in FIG. 9) to be inspected and manually presses the corner positioning members 6, 7 against the adjacent inner wall surfaces (for example, inner wall surfaces A, C).

In this case, if the bottom surfaces of the corner positioning members 6, 7 are not appropriately placed in contact with the adjacent inner wall surfaces, the operator rotates the rotating portions 80 of the testing width adjusting members 8 and adjusts the distances between the coil holding members 4 and 5. As a result, when the bottom surfaces of the corner positioning members 6, 7 are appropriately placed in contact with the adjacent inner wall surfaces, the operator determines that the adjustment of the distances between the coil holding members 4 and 5 or the testing widths has been terminated. Appropriately placing the corner positioning members 6, 7 in contact with the adjacent inner wall surfaces means that the overall bottom surfaces of the corner positioning members 6, 7 are firmly placed in contact with the overall inner wall surfaces.

Next, the operator combines the edge portion testing probes 3 with the central portion testing probes 2 so as to form the eddy current testing probes 1 (in step S11). Specifically, the operator manually engages the protruding portions 17 formed in the coil holding members 5 of the edge portion testing probes 3 with the recessed portions 21 formed in the side surfaces of the central portion testing probes 2, combines the edge portion testing probes 3 with the central portion testing probes 2, and forms the eddy current testing probes 1. In this operation, the operator matches the positions of the bottom surfaces of the coil holding members 4, 5 of the edge portion testing probes 3 with the positions of the bottom surfaces of the central portion testing probes 2.

In this case, frictional forces generated when the protruding portions 17 formed in the coil holding members 5 are engaged with the recessed portions 21 of the central portion testing probes 2 are sufficiently larger than frictional forces required to fix the coil holding members 5 to the central portion testing probes 2. Although the pressing plates 64 of the pressing mechanism carriage 60 press only the upper portions of the casings of the central portion testing probes 2 (refer to FIG. 9), the pressing forces are sufficiently transferred to the coil holding members 5 by the frictional forces generated when the protruding portions 17 of the coil holding members 5 are engaged with the recessed portions 21 of the central portion testing probes 2. Thus, when the pressing plates 64 press the upper portions of the central portion testing probes 2, the bottom surfaces of the central portion testing probes 2 and the bottom surfaces of the coil holding members 4, 5 are placed in contact with the inner wall surfaces (for example, the inner wall surfaces B, B') simultaneously.

Next, the operator inserts the thus-configured eddy current testing probes 1 and the separately prepared pressing mechanism carriage 60 into the slot 91 to be inspected (in step S12) and starts eddy current testing to inspect the inner wall surfaces (for example, the inner wall surfaces B, B') of the slot 91 to be inspected (in step S13). An operation of starting eddy current testing includes an operation of supplying power to the eddy current testing control device 70 and an operation of pressing a testing start button (not illustrated in FIG. 10) provided in the eddy current testing control device 70 or the traveling carriage 62. If the traveling carriage 62 does not have a function of automatically traveling, the operator needs to continue to perform an operation of moving the traveling carriage 62 after the start of eddy current testing.

Figure 12:
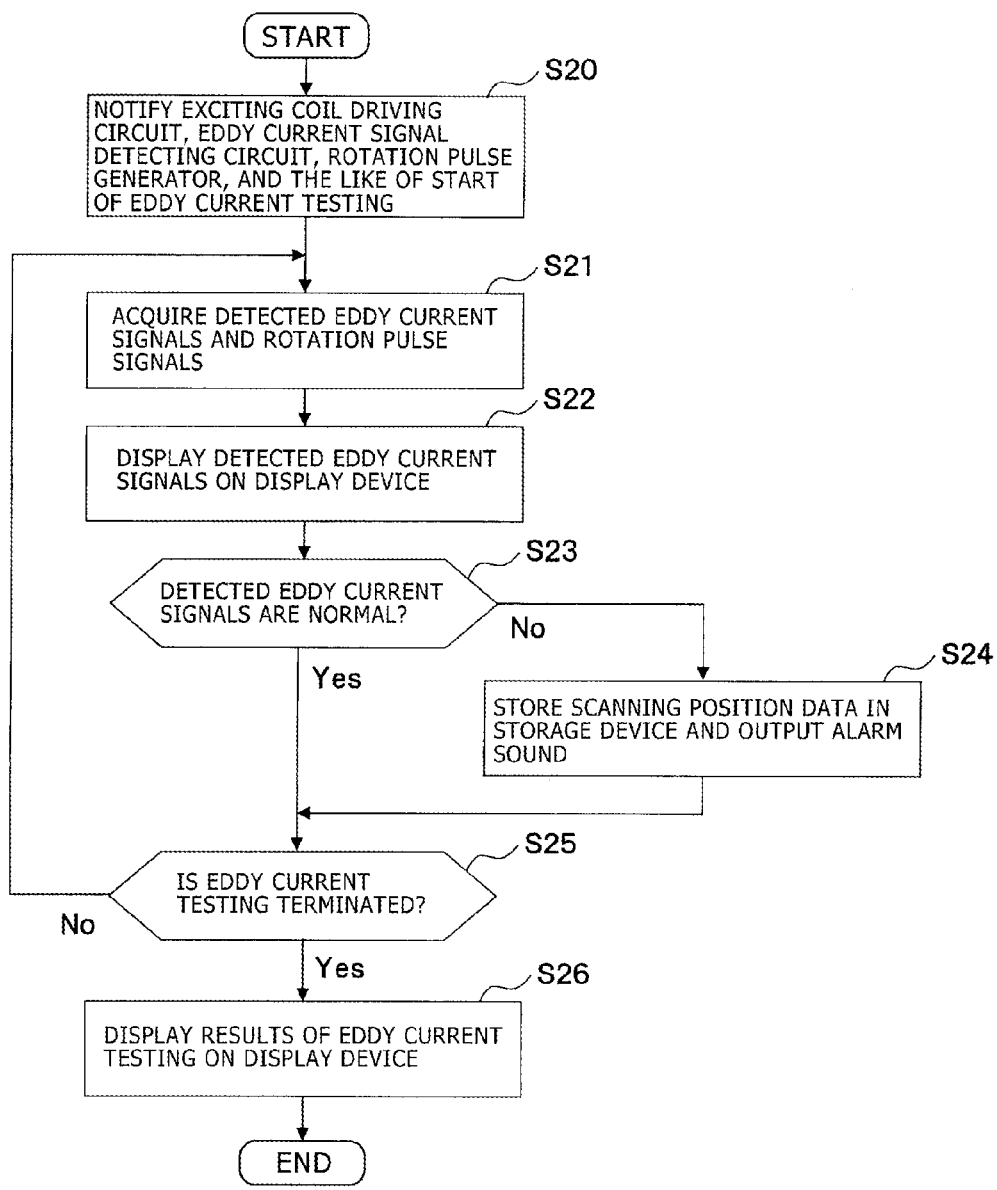
FIG. 12 is a flowchart of an example of an eddy current test control process to be performed by the eddy current testing control device according to the second embodiment of the invention.

FIG. 12 is a flowchart of a process of controlling eddy current testing by the eddy current testing control device 70 according to the second embodiment of the invention. As illustrated in FIG. 12, when the eddy current testing apparatus 100 starts eddy current testing, the data processing device 71 (refer to FIG. 10) of the eddy current testing control device 70 notifies the exciting coil driving circuit 72, the eddy current signal detecting circuit 73, the rotation pulse generator 65, and the like of the start of eddy current testing (in step S20).

When receiving the notification indicating the start of eddy current testing, the exciting coil driving circuit 72 starts to supply an alternating current for excitation to the exciting coils 221 and the eddy current signal detecting circuit 73 starts to cause the detecting coils 222 to detect eddy currents. The rotation pulse generator 65 starts to detect rotations of the wheels 61. If the traveling carriage 62 has the motor for automatic traveling, the data processing device 71 instructs the motor to be activated and causes the motor to start to move the traveling carriage 62.

Next, the data processing device 71 acquires detected eddy current signals from the eddy current signal detecting circuit 73 and acquires rotation pulse signals from the rotation pulse generator 65 (in step S21). In this case, the detected eddy current signals are acquired as voltage signals obtained by converting impedance of the detecting coils 3222 into voltages. The rotation pulse signals are acquired as the numbers of rotations of the wheels and data of rotational angles of the wheels.

Next, the data processing device 71 displays the detected eddy current signals on the display device 76 (in step S22) and determines whether or not the acquired detected eddy current signals are normal (in step S23). If a voltage value acquired as a detected eddy current signal is equal to or lower than a predetermined threshold, the data processing device 71 determines that the detected eddy current signal is normal. If the voltage value exceeds the threshold, the data processing device 71 determines that the detected eddy current signal is abnormal.

If the data processing device 71 determines that a detected eddy current signal is not normal (or is abnormal) (No in step S23), the data processing device 71 causes data of a scanning position of the traveling carriage 62 at the time of the detection of the detected eddy current signal to be stored in a storage device (such as the main memory 712, the HD device 713, or the like) and causes an alarm sound to be output from the audio output device 77 (in step S24). The data of the scanning position of the traveling carriage 62 can be calculated by calculating the diameters of the wheels 61 and the rotation pulse signals (for example, the numbers of rotations of the wheels and the rotational angles of the wheels) acquired from the rotation pulse generator 65.

If the data processing device 71 determines that the detected eddy current signals are normal (Yes in step S23), the data processing device 71 skips the process of step S24 and causes the process to proceed to a process of step S25.

Next, the data processing device 71 determines whether or not eddy current testing is terminated (in step S25). If eddy current testing is not terminated (No in step S25), the data processing device 71 causes the process to return to step S21 and repeats the processes of steps S21 and later. If eddy current testing is terminated (Yes in step S25), the data processing device 71 displays results of eddy current testing on the display device 76 (in step S26) and terminates the process of controlling eddy current testing.

The data processing device 71 recognizes the termination of eddy current testing by detecting that the operator presses a scanning termination button (not illustrated in FIG. 10) provided in the eddy current testing control device 70, the traveling carriage 62, or the like.

In the aforementioned process, if the data processing device 71 detects an abnormality of a detected eddy current signal, the data processing device 71 continues to control eddy current testing. The data processing device 71, however, is not limited to this. If the data processing device 71 detects an abnormality of a detected eddy current signal, the data processing device 71 causes the alarm sound to be output (in step 24) and may immediately terminate the control of eddy current testing after the output of the alarm sound. In this case, a defect exists on or in an inner wall surface (to be inspected) at a position at which eddy current testing is stopped.

Figure 13:
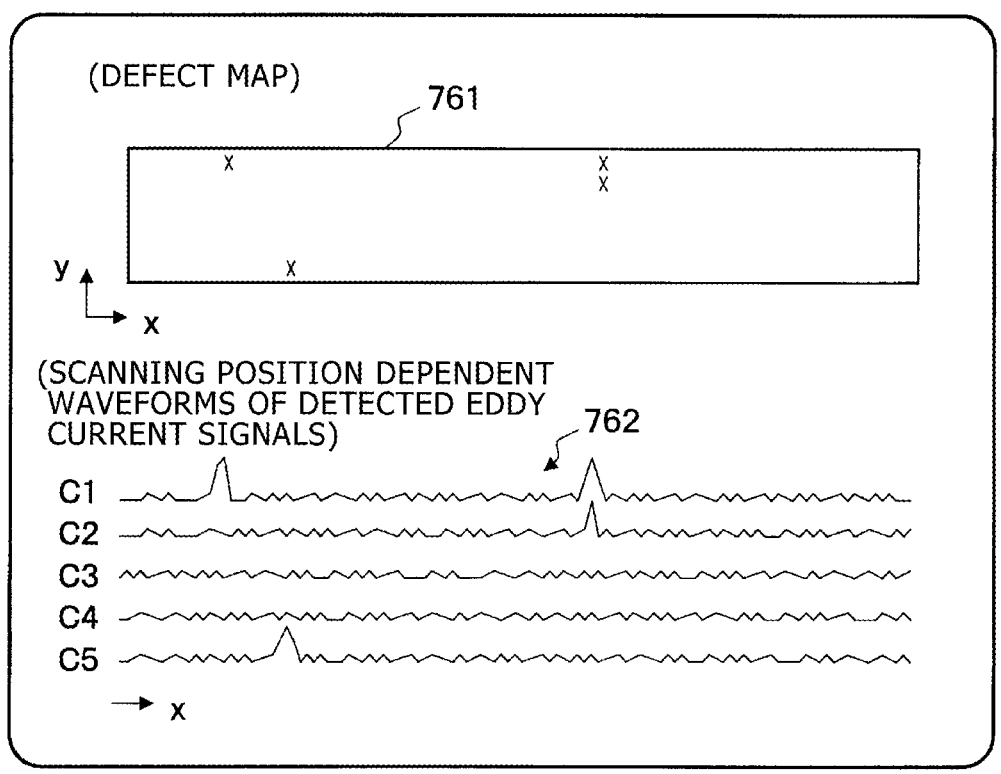
FIG. 13 is a diagram illustrating an example of an eddy current test result display screen displayed on a display device by the eddy current testing control device according to the second embodiment of the invention.

FIG. 13 is a diagram illustrating an example of an eddy current testing result display screen displayed on the display device 76 by the eddy current testing control device 70 according to the second embodiment of the invention. As illustrated in FIG. 13, the results of eddy current testing may be displayed as a defect map 761 or scanning position dependent waveforms 762 of detected eddy current signals.

The defect map 761 is a map in which scanning positions at which abnormalities (defects) of detected eddy current signals are detected are displayed in a flat surface representing an inner wall surface to be inspected. In the defect map 761 illustrated in FIG. 13, x-direction indicates a direction in which the inner wall surface to be inspected is scanned, and y-direction indicates a width direction of the inner wall surface. In the defect map 761, the overall inner wall surface to be inspected is represented by a rectangle, and symbols x are added at the scanning positions at which the defects are detected. The positions of the defects can be clearly recognized by the defect map 761.

The scanning position dependent waveforms 762 of the detected eddy current signals are waveforms formed by associating values (for example, impedance values) of the detected eddy current signals obtained by the plurality of detecting coils 222 with the scanning positions. In FIG. 13, symbols C1 to C5 identify the detecting coils 222, and the abscissa x indicates a position in the scanning direction. The heights of the waveforms indicate the values (for example, impedance values) of the detected eddy current signals. Thus, the sizes and the like of the defects can be estimated in detail by the scanning position dependent waveforms 762 of the detected eddy current signals.

In the second embodiment of the invention, the pressing mechanism carriage 60 that has the wheels 61 is provided in order to press the eddy current testing probes 1 according to the first embodiment against the inner wall surfaces of the slot 91 to be inspected and move the eddy current testing probes 1 according to the first embodiment in the depth direction of the slop 91 while pressing the eddy current testing probes 1 against the inner wall surfaces. In addition, the eddy current testing control device 70 acquires and processes detected eddy current signals acquired when the pressing mechanism carriage 60 travels in the slot 91 to be inspected or the eddy current testing probes 1 scans the inner wall surfaces to be inspected. Thus, burden on the operator during operation can be reduced, and the operator can easily recognize the position and state of a defect.

According to the first and second embodiments of the invention, since dependency on the shape of the slot 91 of the object 9 to be inspected can be reduced, the same eddy current testing probe 1 is applicable to slots 91 having different shapes. Thus, it is not necessary to form the eddy current testing probes 1 for the slots 91 having the different shapes, and the cost and time for the formation can be reduced. It is economical to reduce the cost and time for the formation. Since the eddy current testing probes 1 (edge portion testing probe 3) can reliably contact the corners of the inner wall surfaces (to be inspected) of the slot 91, the performance of detecting a defect can be improved.

Third Embodiment

Figure 14:
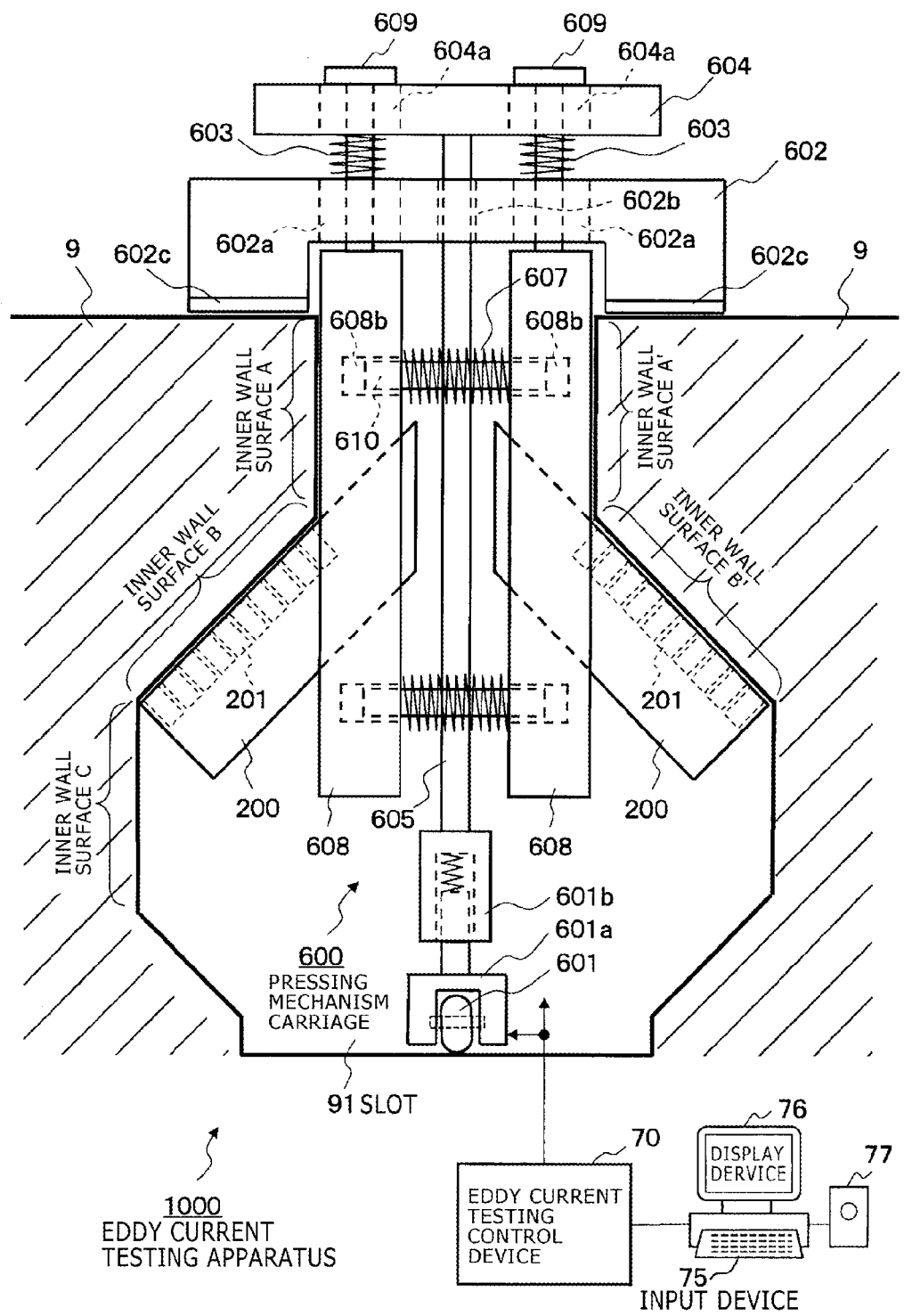
FIG. 14 is a diagram schematically illustrating an example of the configuration of an eddy current testing apparatus according to a third embodiment of the invention and a state in which the eddy current testing apparatus according to the third embodiment is applied to eddy current testing to be performed to inspect the inner wall surfaces of the slot of the object to be inspected.

FIG. 14 is a diagram schematically illustrating an example of the configuration of an eddy current testing apparatus 1000 according to a third embodiment of the invention and a state in which the eddy current testing apparatus 1000 is applied to eddy current testing to be performed to inspect the inner wall surfaces of the slot 91 of the object 9 to be inspected.

The groove-shaped slot 91 is formed in the object 9 to be inspected and is long in the depth direction (direction perpendicular to the sheet of FIG. 14) in the same manner as the first embodiment (refer to FIG. 1) and the second embodiment (refer to FIG. 9). The slot 91 is the space surrounded by the plurality of the flat inner wall surfaces (inner wall surfaces A, B, C and the like) that are long in the depth direction and partitioned by the plurality of corners. It is assumed that a cross-sectional shape of the slot 91 is the same at any position in the depth direction.

As illustrated in FIG. 14, the eddy current testing apparatus 1000 according to the third embodiment of the invention includes eddy current testing probes 200, a pressing mechanism carriage 600, and the eddy current testing control device 70. The pressing mechanism carriage 600 has a mechanism for pressing bottom portions of the eddy current testing probes 200 against the inner wall surfaces that are included in the slot 91 and to be inspected. The eddy current testing control device 70 controls acquisition of eddy current testing data during eddy current testing.

In the example illustrated in FIG. 14, the eddy current testing apparatus 1000 has the two eddy current testing probes 200 that perform eddy current testing to inspect the inner wall surfaces B, B' of the slot 91.

The pressing mechanism carriage 600 includes a traveling carriage 602 and a pressing mechanism. The traveling carriage 602 moves on the upper surfaces of the object 9 that has the slot 91 formed therein and is to be inspected. The pressing mechanism is arranged on the traveling carriage 602 and presses the eddy current testing probes 200 against the inner wall surfaces to be inspected.

The pressing mechanism includes spring members 603, an upper holding plate member 604, two eddy current testing probe holding members 608, and spring members 607. The upper holding plate member 604 is attached to the traveling carriage 602 through the spring members 603. The eddy current testing probe holding members 608 are suspended by the upper holding plate member 604 through bolts 609 and can downwardly extend to the inside of the slot 91. The spring members 607 couple the two eddy current testing probe holding members 608 to each other.

The upper holding plate member 604 is attached to an upper surface of the traveling carriage 602 through the spring members 603 so as to be substantially parallel to surfaces on which the traveling carriage 602 travels or upper surfaces of an outer portion of the object 9 to be inspected. The upper holding plate member 604 has openings 604a through which legs of the bolts 609 extend, while the traveling carriage 602 has openings 602a through which the legs of the bolts 609 extend. The legs of the bolts 609 extend through the openings 604a, the spring members 603, and the openings 602a and reach upper portions of the eddy current testing probe holding members 608, and edges of the legs of the bolts 609 are screwed into and fixed to upper surfaces of the eddy current testing probe holding members 608 (an illustration of portions at which the edges of the legs of the bolts 609 are screwed into the upper surfaces is omitted in FIG. 14).

Upper surfaces of the openings 604a formed in the upper holding plate members 604 and upper surfaces of the openings 602a formed in the traveling carriage 602 are thin and long in the direction in which the inner wall surfaces of the slot 9 extend. The widths (short diameters) of the upper surfaces of the openings 604a and 602a are slightly larger than the diameters of the legs of the bolts 609 and sufficiently smaller than the diameters of heads of the bolts 609. Thus, the eddy current testing probe holding members 608 are suspended by the upper holding plate member 604 through the bolts 609 so as to be slidable in the direction in which the inner wall surfaces of the slot 9 extend.

In this case, the spring members 603 upwardly press the upper holding plate member 604 by compression repulsive forces of the spring members 603. Thus, the eddy current testing probe holding members 608 receives the upward forces.

Holes 608b are formed at the same positions in surfaces of the two eddy current testing probe holding members 608, while the surfaces face each other. Bars 610 can be inserted into and extracted from the holes 608b. Both ends of each of the bars 610 that hold the spring members 607 compressed are inserted into the holes 608b formed in the two eddy current testing probe holding members 608 and facing each other. Thus, the spring members 607 press the two eddy current testing probe holding members 608 by compression repulsive forces of the spring members 607 in a horizontal direction (left-and-right direction in FIG. 14 or toward the inner wall surfaces of the slot 91).

The eddy current testing probe holding members 608 hold the eddy current testing probes 200 that perform eddy current testing to inspect the inner wall surfaces B, B' of the slot 91. The eddy current testing probes 200 have coils 201 for eddy current testing on bottom portions (facing obliquely upward in FIG. 14) of the eddy current testing probes 200, while the bottom portions of the eddy current testing probes 200 are placed in contact with the inner wall surfaces B, B'.

Since the thus-configured pressing mechanism is provided, the eddy current testing probes 200 that are held by the eddy current testing probe holding members 608 receive the forces applied by the spring members 603 in the upward direction and the forces applied by the spring members 607 in the horizontal direction (left- and right-direction). Thus, the two eddy current testing probes 200 receive a force applied in a left and obliquely upward direction and a force applied in a right and obliquely upward direction, respectively. The bottom portions of the two eddy current testing probes 200 are pressed against and placed in contact with the inner wall surfaces B, B', while the eddy current testing probe holding members 608 are pressed against and placed in contact with the inner wall surfaces A, A'.

Referring to FIG. 14, a descending holding plate member 605 that deeply extends to the inside of the slot 91 is attached and fixed to a central portion of the upper holding member 604. An opening 602b through which the descending holding plate member 605 extends is formed in a central portion of the traveling carriage 602.

A wheel holding portion 601a and a wheel pressing portion 601b are provided at a lower portion of the descending holding plate member 605. The wheel holding portion 601 holds a wheel 601. The wheel pressing portion 601b presses the wheel 601 from the upper side to the lower side by a spring member or the like. The descending holding plate member 605 holds the wheel holding portion 601a and the wheel pressing portion 601b from the upper side.

The wheel 601 plays a role of measuring a travel distance of the traveling carriage 602, rather than holding the traveling carriage 602 through the descending holding plate member 605 on the bottom surface of the slot 91. Thus, the rotation pulse generator 65 (refer to FIG. 10) such as a rotary encoder is provided for the wheel 601.

In the present embodiment, the traveling carriage 602 has sliding portions 602c instead of wheels for holding the carriage. The sliding portions 602c are placed in contact with the upper surfaces of the object 9 (to be inspected) provided with the slot 91. Thus, the sliding portions 602c are made of a material (such as fluoride resin) having low frictional resistance to the upper surfaces of the object 9 to be inspected.

In the third embodiment, the eddy current testing control device 70 that includes the input device 75 (such as a keyboard, a mouse, a touch panel, or the like), the display device 76 (such as a liquid crystal display device), and the audio output device 77 (such as a speaker) is used, like the second embodiment (refer to FIG. 9). The configuration of the eddy current testing control device 70 is described above with reference to FIG. 10, and a description thereof is omitted.

FIGS. 15A and 15B are a front view and a left side view that schematically illustrate an example of a structure in which the eddy current testing probe 200 is held by the eddy current testing probe holding member 608 in the eddy current testing apparatus 1000 according to the third embodiment of the invention.

As illustrated in FIGS. 15A and 15B, the eddy current testing probe holding member 608 has an opening 608a extending therethrough and formed in a central portion of the eddy current testing probe holding member 608, and the eddy current testing probe 200 is engaged with and fixed to the opening 608a.

In this case, upper and lower surfaces of the opening 608a are inclined with respect to a flat surface perpendicular to a vertical axis of the eddy current testing probe holding member 608, and the inclination angle is set to be equal to inclination angles of the inner wall surfaces B, B'. Specifically, when the eddy current testing probe 200 is engaged with the opening 608a of the eddy current testing probe holding member 608, an angle formed between the bottom surface of the eddy current testing probe 200 and the vertical axis of the eddy current testing probe holding member 608 is equal to an angle formed between the inner wall surfaces B, B' and the inner wall surfaces A, A'.

As described with reference to FIG. 14, the coils 201, 202 (an illustration of the coils 202 is omitted in FIGS. 14 and 15A) for eddy current testing are arranged on the bottom portions of the eddy current testing probes 200 placed in contact with the inner wall surfaces B, B'. The width L of a region in which the coils 201, 202 are arranged or the length L of a bottom surface portion included in the eddy current testing probe 200 and protruding from the opening 608a of the eddy current testing holding member 608 is set to be equal to the widths of the inner wall surfaces B, B'.

Thus, the eddy current testing probe holding members 608 are pressed against and almost exactly placed in contact with the inner wall surfaces A, A', while the eddy current testing probes 200 are pressed against and almost exactly placed in contact with the inner wall surfaces B, B'.

In FIGS. 15A and 15B, the positions of the holes 608b in which the ends of the bars 610 that hold the spring members 607 are inserted are indicated by broken lines. As is apparent from FIGS. 14, 15A, and 15B, the two eddy current testing probe holding members 608 are pressed against and coupled to each other through the four bars 610 that hold the spring members 607. In FIG. 15B, the four holds 608b are formed in each of the eddy current testing probe holding members 608, or the two eddy current testing probe holding members 608 are coupled to each other through the four bars 610 holding the spring members 607. The number of the bars 610, however, is not limited to four.

FIGS. 16A and 16B are top and front views schematically illustrating an example of the structure of the eddy current testing probe 200 used in the eddy current testing apparatus 1000 according to the third embodiment of the invention.

As illustrated in FIGS. 16A and 16B, the eddy current testing probe 200 includes the coils 201 and the coils 202 on the bottom portion of the eddy current testing probe 200. The coils 202 are arranged in an array and can perform eddy current testing to inspect the inner wall surfaces B, B' (to be inspected) across the overall widths of the inner wall surfaces B, B'. The coils 202 are arranged to perform eddy current testing to inspect the edges of the inner wall surfaces B, B' with high accuracy. In FIG. 16B, an illustration of the coils 202 is omitted.

When the coils 201, 202 arranged in the eddy current testing probe 200 illustrated in FIGS. 16A and 16B are associated with the coils 11, 12, and 22 arranged in the eddy current testing probe 1 (illustrated in FIGS. 2A to 3B) according to the first embodiment, the coils 201 correspond to the coils 22 (refer to FIGS. 3A and 3B) arranged in the central portion testing probe 2, and the coils 202 correspond to the coils 11, 12 (refer to FIGS. 2A and 2B) arranged in the edge portion testing probe 3.

The coils 201 arranged in the array in the eddy current testing probes 200 may be replaced with the exciting coils 40, 46, 51, or 56 (illustrated in FIGS. 5A to 8B) and the detecting coils 41, 47, 52, or 57 (illustrated in FIGS. 5A to 8B). In addition, the coils 202 that are arranged to perform eddy current testing to inspect both edges of each of the inner wall surfaces B, B' may not be arranged.

A method for performing eddy current testing to inspect the inner wall surfaces B, B' (to be inspected) using the eddy current testing apparatus 1000 described with reference to FIGS. 14 to 16B is almost the same as the method described with reference to FIGS. 11 to 13, and a description thereof is omitted.

According to the third embodiment of the invention, since the eddy current testing probes 200 that are pressed against the inner wall surfaces of the slot 91 by the pressing mechanism are configured so that the positions and inclination angles of the eddy current testing probes 200 attached to the eddy current testing probe holding members 608 conform to the shapes of specific inner wall surfaces (for example, the inner walls surfaces B, B' or the like) to be inspected, the accuracy of eddy current testing performed by the eddy current testing probes 200 can be improved.

According to the third embodiment of the invention, even if the widths or inclination angles of the inner walls surfaces (for example, the inner wall surfaces B, B') to be inspected vary, the eddy current testing apparatus 1000 does not need to be newly formed, and it is sufficient if only the eddy current testing probe holding members 608 and eddy current testing probes 200 that are simple structural parts are remade. Thus, it can be said that the eddy current testing apparatus 1000 according to the third embodiment of the invention has a structure that easily supports a variation in the structure of an inner wall surface of the slot 91 to be inspected.

In the third embodiment of the invention, the traveling carriage 602 is placed outside the slot 91. Thus, when eddy current testing is performed using the eddy current testing apparatus 1000 to inspect specific inner wall surfaces (for example, the inner wall surfaces B, B') of the slot 91, the operator that performs eddy current testing can manually push and pull the traveling carriage 602 and thereby freely move the eddy current testing apparatus 1000. This means that the operability of the eddy current testing apparatus 1000 for the operator is improved.

First Modified Example of Third Embodiment

In the description using FIGS. 15A and 15B, the eddy current testing probes 200 are engaged with and fixed to the openings 608a of the eddy current testing probe holding members 608, and the widths L of the regions in which the coils 201, 202 are arranged on the bottom surfaces of the eddy current testing probes 200 are set to be equal to the widths of the inner wall surfaces B, B'. This means that the eddy current testing apparatus 1000 cannot be applied to eddy current testing of other objects 9 (to be inspected) provided with slots 91 of which the widths of inner wall surfaces B, B' are different from each other.

In the first modified example, the eddy current testing probes 200 can be engaged with and fixed to the openings 608a of the eddy current testing probe holding members 608 at arbitrary positions.

In order to achieve this, when the eddy current testing probes 200 are tightly engaged with the openings 608a, and the eddy current testing probes 200 and the eddy current testing probe holding members 608 are pressed against the inner wall surfaces of the slot 91, it is sufficient if the positions at which the eddy current testing probes 200 are engaged are not changed. In order not to change the positions at which the eddy current testing probes 200 are engaged, the eddy current testing probes 200 may be fixed at arbitrary positions of the openings 608a.

The widths L of the regions in which the coils 201, 202 are arranged in the eddy current testing probes 200 may be set to a large value.

By performing the setting in the aforementioned manner, the eddy current testing apparatus 1000 according to the first modified example is applicable to a plurality of objects 9 (to be inspected) provided with slots 91 of which the widths of inner wall surfaces B, B' to be inspected are different from each other. In the first modified example, when the widths of the inner wall surfaces B, B' to be inspected vary, the eddy current testing probes 200 are pushed into and pulled from the openings 608a of the eddy current testing probe holding members 608 so that the lengths L of the bottom surface portions included in the eddy current testing probes 200 and protruding from the openings 608a match the widths of the inner wall surfaces B, B'.

The applicability of the eddy current testing apparatus 1000 according to the first modified example to a difference between cross-sectional shapes of slots 91 to be inspected can be improved.

In the first modified example, the fact that the distance between the two coils 202 is fixed does not mean that the accuracy of performing eddy current testing to inspect both edges of each of the inner wall surfaces B, B' to be inspected is improved, and the coils 202 may be omitted. In this case, in order to improve the accuracy of performing eddy current testing to inspect parts including both edges of each of the inner wall surfaces B, B' to be inspected, the coils 201 that are arranged in the array may be arranged in two rows in each of the eddy current testing probes 200.

Second Modified Example of Third Embodiment

Figures 17A, 17B:
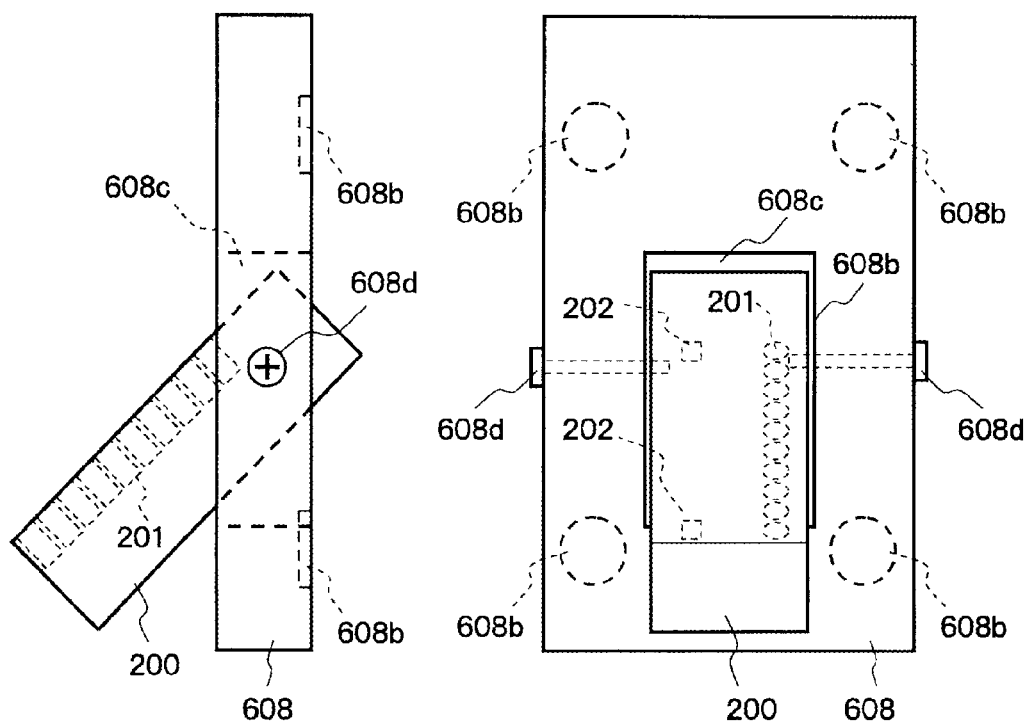
FIGS. 17A and 17B are a front view and a left side view that schematically illustrate an example of a structure in which the eddy current testing probe is held by the eddy current testing probe holding member in a second modified example of the third embodiment of the invention.

FIGS. 17A and 17B are a front view and a left side view that schematically illustrate an example of a structure in which the eddy current testing probe 200 is held by the eddy current testing probe holding member 608.

In the third embodiment illustrated in FIGS. 15A and 15B, the eddy current testing probe 200 is engaged with the opening 608a of the eddy current testing probe holding member 608, and an angle formed between the bottom surface of the eddy current testing probe 200 and the vertical axis of the eddy current testing probe holding member 608 is fixed and cannot be changed. This means that the eddy current testing apparatus 1000 is not applicable to eddy current testing of other objects 9 (to be inspected) provided with slots 91 of which inclination angles of inner wall surfaces B, B' are different from each other.

To avoid this, the opening 608a of the eddy current testing probe holding member 608 is set to be relatively large, and the eddy current testing probe 200 is held by a screw member 608d and can be freely rotated in a certain angular range in the opening 608a in the second modified example as illustrated in FIGS. 17A and 17B. Thus, the angle formed between the bottom surface of the eddy current testing probe 200 and the vertical axis of the eddy current testing probe holding member 608 can be freely set and fixed by firmly tightening the screw member 608d.

According to the second modified example, the angles formed between the bottom surfaces of the eddy current testing probes 200 and the surfaces, contacting the inner wall surfaces of the slot 91, of the eddy current testing probe holding members 608 can match the angles formed between the inner wall surfaces B, B' of the slot 91 and the inner wall surfaces A, A' of the slot 91.

Thus, the applicability of the eddy current testing apparatus 1000 according to the second modified example to a difference between cross-sectional shapes of slots 91 to be inspected can be improved.

It is to be noted that the present invention is not limited to the aforementioned embodiments, but covers various modifications. While, for illustrative purposes, those embodiments have been described specifically, the present invention is not necessarily limited to the specific forms disclosed. Thus, partial replacement is possible between the components of a certain embodiment and the components of another. Likewise, certain components can be added to or removed from the embodiments disclosed.

What is claimed is:

1. An eddy current testing apparatus comprising:
an eddy current testing probe having an eddy current testing coil arranged on a bottom portion of a casing;
a pressing mechanism configured to press the eddy current testing probe so that the bottom portion of the eddy current testing probe is placed in contact with a part of an inner wall surface of a slot formed in an object to be inspected;
a carriage configured to mount the pressing mechanism and the eddy current testing probe, the carriage traveling in a depth direction of the slot; and
an eddy current testing control device configured to control defect detection for the inner wall surface of the slot by acquiring a detected eddy current signal from the eddy current testing coil;
wherein the carriage travels along the slot on an outer upper surface of the object to be inspected while being held by the outer upper surface of the object having the slot formed therein,
the pressing mechanism mounted on the carriage includes a first spring member,
a second spring member,
a holding plate member attached to the carriage through the first spring member, and
two eddy current testing probe holding members suspended by the holding plate member and downwardly extended from the holding plate member to the inside of the slot, the two holding member being coupled to each other by the second spring member and each configured to hold the eddy current testing probes,
the first spring member upwardly presses the holding plate member and the two eddy current testing probe holding members suspended by the holding plate member by a compression repulsive force of the first spring member, and
the second spring member presses the two eddy current testing probe holding members by a compression repulsive force of the second spring member against the inner wall surfaces included in the slot, the inner wall surfaces being substantially opposed to each other.

2. An eddy current testing apparatus comprising:
an eddy current testing probe having an eddy current testing coil arranged on a bottom portion of a casing;
a pressing mechanism configured to press the eddy current testing probe so that the bottom portion of the eddy current testing probe is placed in contact with a part of an inner wall surface of a slot formed in an object to be inspected;
a carriage configured to mount the pressing mechanism and the eddy current testing probe, the carriage traveling in a depth direction of the slot; and
an eddy current testing control device configured to control defect detection for the inner wall surface of the slot by acquiring a detected eddy current signal from the eddy current testing coil;
wherein the carriage includes a wheel and a rotation pulse generator that generates a pulse on the basis of a rotational amount of the wheel.

3. An eddy current testing probe comprising:
a first coil holding member having a plurality of eddy current testing coils arranged on a bottom portion of a casing; and
a second coil holding member having one or more eddy current testing coils arranged on bottom portions of both edges of the casing, the second coil holding member being attached to contact with a side surface of the casing and the second coil holding member being detachable, wherein:
the second coil holding member has a length adjusting member for adjusting a distance between both end portions of the second coil holding member.

4. The eddy current testing probe according to claim 3, wherein:
the second coil holding member has rotary shafts perpendicular to the side surface of the casing arranged at the end portions thereof, the rotary shafts including corner positioning members with flat bottoms configured to freely rotate around the rotary shafts.

5. The eddy current testing probe according to claim 3, wherein:
the plurality of eddy current testing coils held by the first coil holding member are array coils arranged in substantially parallel to the side surface of the casing.

6. The eddy current testing probe according to claim 3, further comprising:
an electronic switching circuit configured to switch each of the plurality of eddy current testing coils held by the first coil holding member between an exciting coil and a detecting coil.

7. The eddy current testing probe according to claim 3, wherein:
the plurality of eddy current testing coils held by the first coil holding member are at least one exciting coil and at least one detecting coil.

8. The eddy current testing probe according to claim 7, wherein:
the exciting coil is a coil wound around a magnetic body having a gap on the side of the bottom surface of the casing, and the detecting coil is arranged at the gap.

9. An eddy current testing method comprising the steps of:
acquiring, by an eddy current testing apparatus, a detected eddy current signal from an inner wall surface through an eddy current testing probe while a carriage traveling along a slot in a depth direction of the slot; and
outputting, by an eddy current testing apparatus, an alarm sound upon a detection of an abnormality of the acquired detected eddy current signal,
wherein the eddy current apparatus comprises:
an eddy current testing probe includes an eddy current testing coil arranged on a bottom portion of a casing,
a pressing mechanism configured to press the eddy current testing probe so that the bottom portion of the eddy current testing probe is placed in contact with a part of an inner wall surface of a slot formed in an object to be inspected;

a carriage configured to mount the pressing mechanism and the eddy current testing probe to travel in a depth direction of the slot; and an eddy current testing control device configured to control defect detection for the inner wall surface of the slot by acquiring a detected eddy current signal from the eddy current testing coil, wherein the carriage has a wheel and a rotation pulse generator that generates a pulse based on a rotational amount of the wheel; and upon a detection of an abnormality of the detected eddy current signal, the eddy current testing apparatus configured to:

calculate a travel distance of the carriage until the time of the detection of the abnormality on the basis of a rotational amount, angle, and diameter of a wheel, each acquired from the rotation pulse generator, store the travel distance as positional information of a defect, and cause a display device to display the positional information of the defect on a map.

* * * * *